United States Patent [19]

Murray et al.

[11] Patent Number: 5,013,769
[45] Date of Patent: May 7, 1991

[54] METHOD OF MAKING A HYDROGEL-FORMING WOUND DRESSING OR SKIN COATING MATERIAL

[75] Inventors: Douglas G. Murray, Willowdale; Dennis C. Smith, Toronto; James E. Guillet, Don Mills, all of Canada

[73] Assignee: Medipro Sciences Limited, Ontario, Canada

[21] Appl. No.: 475,884

[22] Filed: Feb. 6, 1990

Related U.S. Application Data

[62] Division of Ser. No. 234,726, Aug. 22, 1988, Pat. No. 4,920,158.

[51] Int. Cl.$^5$ ..................... C08L 33/02; C08L 29/04
[52] U.S. Cl. ................................... 523/111; 523/105; 524/22; 524/29; 524/52; 524/377; 424/78; 424/81; 424/484; 424/486; 424/488; 424/80
[58] Field of Search ................ 424/78, 81; 523/111, 523/105; 524/22, 29, 52, 377

[56] References Cited

U.S. PATENT DOCUMENTS

| | | |
|---|---|---|
| 3,579,628 | 5/1971 | Gander et al. ............... 424/445 |
| 3,624,224 | 11/1971 | Watchung . |
| 3,632,754 | 1/1972 | Balassa . |
| 3,639,575 | 2/1972 | Schmolka . |
| 3,730,960 | 5/1973 | Watchung . |
| 3,740,421 | 6/1973 | Schmolka . |
| 3,903,268 | 9/1975 | Balassa . |
| 3,911,116 | 10/1975 | Balassa . |
| 3,914,413 | 10/1975 | Balassa . |
| 3,987,000 | 10/1976 | Gleichenahagan . |
| 4,066,584 | 1/1978 | Allen . |
| 4,265,233 | 5/1981 | Sugitachi et al. . |
| 4,383,022 | 5/1983 | Berger . |
| 4,572,906 | 2/1986 | Sparkes et al. . |
| 4,659,572 | 4/1987 | Murray . |
| 4,750,482 | 6/1988 | Sieverding . |
| 4,767,619 | 8/1988 | Murray . |

FOREIGN PATENT DOCUMENTS

| | | |
|---|---|---|
| 694514 | 9/1964 | Canada . |
| 1202904 | 4/1986 | Canada . |

OTHER PUBLICATIONS

Chemical Abstracts 90 No. 192583v (1979).
Chemical Abstracts 62 No. 7968f (1965).

*Primary Examiner*—Paul R. Michl
*Assistant Examiner*—John J. Guarriello
*Attorney, Agent, or Firm*—Nixon & Vanderhye

[57] ABSTRACT

The invention disclosed is a hydrogel-forming wound dressing or skin coating material suitable for household and veterinary use, consisting substantially entirely of wound-compatible and skin-compatible ingredients and comprising a first hydrophilic polymer, selected from polymers or copolymers of acrylic acid, polymers or copolymers of methacrylic acid, polymers or copolymers of itaconic acid, polymers or copolymers of maleic acid and polymers or copolymers of 3-butene-1,2,3-tricarboxylic acid, or combinations thereof, a second hydrophilic polymer which is capable of interacting with the first polymer to produce, upon drying, a hydrogel of improved water resistance and film forming properties relative to the first polymer alone and water. This material is film forming and substantially transparent but capable of being made opaque.

19 Claims, No Drawings

METHOD OF MAKING A HYDROGEL-FORMING WOUND DRESSING OR SKIN COATING MATERIAL

This is a division of application Ser. No. 07/234,726, filed 22 Aug. 1988 now U.S. Pat. No. 4,920,158.

FIELD OF THE INVENTION

This invention relates to a wound dressing or skin coating material suitable for household and veterinary use for application to minor cuts, burns, abrasions, lesions and the like and for application to healthy skin. More particularly, the invention relates to hydrogel-forming wound dressing materials which can be self-applied or applied by an untrained person and similarly removed.

BACKGROUND OF THE INVENTION

In order to allow the healing of lesions to take place at an appropriate rate and without undue pain, an appropriate coverage is placed over the affected area.

It is desirable that this coverage or dressing material constitute ingredients that are all compatible with human or animal skin, and provide, between the environment and the wound, an effective transmission of moisture, while specifically excluding microorganisms from the wound site.

It would be advantageous for such a preparation to be very quick drying, otherwise the home-user or clinician will not have the patience to use it, nor in many cases the opportunity, especially where children or animals are involved.

Another advantageous property of this dressing would be transparency, not only for cosmetic reasons but also to permit inspection of the healing process. Ideally, it should also be capable of being applied as very thin layers so that the resulting dressing would not be cumbersome.

It is also desired that such a dressing be easy to apply and remove, aesthetically pleasing, and non-odourous.

Although such a preparation encompassing all of the above advantages is not presently available, there is a genuine demand for it in many areas including the health care delivery area.

A wide variety of products are currently available on the market in the field of wound dressings. For example, sterile gauze-type dressings that are arranged in strips of various shapes and can be applied directly to the wound, are widely employed in the home for minor injuries. These dressings are mounted on plastic or fabric strips, with an adhesive coating for attachment to skin. Gauze pads are frequently covered with a perforated plastic strip to prevent adhesion of gauze to the wound surface.

U.S. Pat. No. 4,616,644, which issued to Johnson and Johnson Products, discloses a hemostatic adhesive bandage which comprises a pressure-sensitive adhesive-coated backing attached to an absorbent pad covered with a perforated plastic film wound release cover, the wound release cover having a thin coating of polyethylene oxide.

Despite their wide acceptance, the gauze-type dressings are not without their disadvantages. For instance, frequent and sometimes painful changes of such dressings are necessary in order to observe that the healing process is proceeding as desired, and to renew medication. These traditional dressings include two disposable strips called "release sheets" to protect the adhesive, which when removed, present a litter disposal problem. They are usually in strips which are difficult to scale to the size and shape of the individual wounds, especially between fingers and on joints. When applying these preparations to the fingers, it is often necessary to wrap the dressing around several times, so that despite the fact that they are semi-permeable, moisture may not be able to escape adequately leaving the wound site and healthy skin around the wound site swollen and lighter in colour. Moreover, wetting of these gauze-type dressings results in a retained water layer which favours microbial growth. Some manufacturers, such as Johnson and Johnson, have addressed this problem by incorporating an anti-microbial agent, such as benzalkonium chloride, into the gauze pad.

Hydrogels are apparently solid materials, which have some characteristics of animal skin and presumably would provide a good basis for wound dressings. According to Joseph D. Andrade in *Hydrogels for Medical and Related Applications,* A.C.S. Symposium Series 31, American Chemical Society, 1976, page xi, hydrogels "are three-dimensional networks of hydrophilic polymers, generally covalently or ionically cross-linked, which interact with aqueous solutions by swelling to some equilibrium value". It is known, in some instances, that complexing or interaction between polymer chains occurs by way of hydrogen bonding to form a hydrogel.

It is known to use hydrogel preparations for the clinical treatment of wounds, in particular severe burns. U.S. Pat. No. 4,572,906 discloses a selfsupporting film for use as a surgical dressing in the treatment of severe burns, comprising the hydrogel (15% water) blend of gelatin, chitosan and a compatible plasticizer. The dressing may be removed from the wound by soaking in physiological saline or water.

Canadian Pat. No. 1,176,932 also relates to a hydrogel-based wound adherent film for surgical application consisting of gelatin and a water soluble resin such as polyethylene oxide or polyethylene imine.

Canadian Pat. No. 1,180 622 discloses a hydrogel similar to Canadian Patent No. 1,176,932; however, the combination of gelatin and water soluble resin is in a liquid preparation to be poured by a skilled surgeon directly onto the wound as opposed to existing as a preformed film.

Although these hydrogel preparations provide good protection for wounds, allowing transmission of water vapour from the wound, generally cause less trauma of the skin surrounding the wound after removal (lightness of colour, swelling) compared to conventional dressings, and are transparent allowing the surgeon to monitor the progress of the healing, they do not lend themselves to household use. These hydrogel wound dressings contain, in some instances (Canadian Pat. Nos. 1,180,622 and 1,176,932) ingredients having systemic toxicity such as polyethylene imine. These dressings are therefore suitable for human use only when applied by or under the supervision of a professional for application to large areas of human tissue. For application to smaller areas, self-application may, in some instances, be possible. These preparations are also insufficiently quick-drying for household use.

Other dressings useful in surgical application include those of U.S. Pat. No. 4,524,064 and U.S. Pat. No. 4,243,656.

U.S. Pat. No. 4,524,064 to Nambu discloses a wound covering comprising polyvinyl alcohol, a water-soluble polyhydric alcohol and a high-viscosity water-soluble macromolecular substance. This latter ingredient provides high viscosity for the covering which interferes with migration of the covering components. It is recited in the disclosure of this patent that only high-viscosity macromolecular substances may be used, with the exception of polyvinyl alcohol and a list is given which includes polyacrylic acid. In this instance, polyacrylic acid is employed in a very small amount, and does not provide adhesion to the coating. It is merely added as a viscosity builder.

U.S. Pat. No. 4,243,656 to Walliczek discloses a paint-on liquid dressing for first and second degree burns consisting of acrylic polymer, gelatin, glycerol and water. The acrylic polymer is in the form of an emulsion and is not hydrogel-forming. Accordingly, although gelatin is hydrogel-forming, it merely acts to dilute the emulsion which, when applied to the skin, collapses due to evaporation of water. The emulsion, once collapsed, is not entirely hydrophobic, that is it will absorb some water although it is to such a small extent that it is outside the conventional recognized definition of a hydrogel.

It is known to utilize hydrogel wound dressings for the household treatment of wounds. Two alleged household wound dressings are disclosed in U.S. Pat. No. 3,419,006. These preparations, composed of hydrophilic, polymeric gels are almost entirely water (i.e. approximately 96% water), which leads to poor adhesion to the wound site. They must be reinforced with nylon mesh to prevent breakage. These preparations are primarily intended for use as shoe inserts to prevent chaffing against the skin.

It is an object of this invention to provide an inexpensive wound dressing material that contains only wound compatible ingredients to allow household and clinical use of such a preparation, allows effective transmission of water vapour from the wound site, and provides an effective barrier for the wound against exogenous microorganisms.

It is another object of this invention to provide an aesthetically pleasing, wound dressing material that is relatively quick-drying and transparent, although capable of being made opaque, and is easy to apply to allow self-application or application by an untrained person and similar easy removal.

It is another object of the present invention to provide a skin coating material.

SUMMARY OF THE INVENTION

According to the present invention, there is provided a hydrogel-forming wound dressing or skin coating material consisting substantially entirely of wound-compatible and skin-compatible ingredients and comprising a first hydrophilic polymer selected from polymers or copolymers of acrylic acid, polymers or copolymers of methacrylic acid, polymers or copolymers of itaconic acid, polymers or copolymers of maleic acid, and polymers or copolymers of 3-butene-1,2,3-tricarboxylic acid, or combinations thereof; a second hydrophilic polymer which is capable of interacting with the first polymer to produce, upon drying, a hydrogel of improved water resistance and film-forming properties relative to the first hydrophilic polymer alone; and water; the material being film-forming and substantially transparent or translucent although capable of being made opaque.

This non-toxic wound dressing material allows, between the wound and the environment, transmission of water vapour to facilitate wound healing It also provides a suitable barrier for the wound against microorganisms including some viruses, which may lead to infection and therefore delay the healing process.

The term "wound-compatible" referred to herein, describes materials which can be applied to a flesh wound site of a human or other animal and will be compatible with the wound site and surrounding flesh, and will not deleteriously interfere with the normal healthy biological processes encountered at the wound site. In the instances where this dressing is used as a skin coating, in such applications as an insect repellent, a sunscreen or a fragrance vehicle, the term "skin compatible" means not deleterious to normal, healthy skin on which it is applied.

The wound dressing or skin coating material described herein is relatively quick-drying to provide the convenience necessary for household use, and may be substantially transparent which makes the material not only aesthetically appealing but also permits the inspection of the healing process without dressing removal.

Although transparency in most instances, is a desirable feature in a wound dressing preparation, an additional embodiment of this invention, described hereinbelow, discloses an opaque wound dressing or skin coating material for use on occasions when opacity or non-transparency is desired.

After removal of the material according to the invention from the wound site, the skin surrounding the wound area is relatively free from the swelling and lightness of colour which results from use of traditional dressings. The elimination of these problems is due, in part, to the enhanced water vapour transmission of the dressing of the present invention. Moreover, this dressing may be applied from a tube, so as to avoid immediate litter disposal problems.

This preparation, since it forms a hydrogel, may, while maintaining a water concentration equilibrium with the air, swell and absorb many times its weight in water. It is compatible with normal human and animal skin and is capable of conforming to skin contours and folds to allow application to finger and elbow joints.

The wound dressing material described herein may effectively be applied to minor cuts, burns, abrasions, dermatological disorders such as enzema and acne, and may be used in the treatment of warts.

It is also contemplated within the scope of the present invention that the skin-coating materials described herein may be used as insect repellents, sunscreens and vehicles for the controlled release of fragrances such as perfume and cologne.

PREFERRED EMBODIMENTS

In a preferred form of this invention, a hydrogel-forming wound dressing or skin-coating for application directly to the wound, or to areas of healthy skin, consisting substantially entirely of wound-compatible ingredients, is prepared comprising a first hydrophilic polymer selected from polymers or copolymers of acrylic acid (PAA), polymers or copolymers of methacrylic acid (PMA), polymers or copolymers of itaconic acid (PIA), polymers or copolymers of maleic acid (PLA) and polymers or copolymers of 3-butene-1,2,3-tricarboxylic acid (PBA), or combinations thereof, a second hydrophilic polymer selected from polyvinyl alcohol (PVA), polyvinyl pyrrolidone (PVP), polyethylene oxide (PEO), copolymer combinations of propylene oxide and ethylene oxide [P(EO/PO)], and gelatin; and water. This material, when applied as a liquid, dries in situ on the wound and adjacent healthy skin to a continuous film that will withstand immersion in sea or tap water or normal washing, as well as overcoatings with hand creams and waterless hand cleaners. This material will allow relatively free movement of the area containing the wound, and will permit a generous transmission of water vapour from the wound site while providing a barrier to microorganisms including some viruses.

It is preferred although not strictly necessary in all embodiments, that at least one suitable plasticizer be added to the hydrogel-forming material.

One preferred embodiment of this invention is a wound dressing or skin-coating material for application to minor cuts, burns, abrasions, lesions and the like, comprising effective amounts of polymers or copolymers of acrylic acid, polymers or copolymers of methacrylic acid, polymers or copolymers of itaconic acid, polymers or copolymers of maleic acid or polymers or copolymers of 3-butene-1,2,3-tricarboxylic acid, or combinations thereof as first hydrophilic polymer, polyvinyl alcohol as second hydrophilic polymer, suitable plasticizer(s) and water.

Polyvinyl alcohol (PVA), prepared by hydrolysis of polyvinyl acetate, falls into two main, useful commercial grades: "fully hydrolyzed" (98+mole % hydrolyzed) or "partially hydrolyzed" (87–89 mole % hydrolyzed). Both fully and partially hydrolyzed grades are water soluble but the fully hydrolyzed grade should normally be heated to 80° C. or higher before it will dissolve. Fully hydrolyzed grades of PVA are present in the composition to enhance water resistance. When immersed in water, fully hydrolyzed grades of PVA swell in length and width substantially more than partially hydrolyzed grades. The increase in length and width creates a shear force which promotes dislodgement of the swollen dressing. A mixture of fully and partially hydrolyzed grades is therefore preferred. Low molecular weight PVA is used to maximize the solids level in the composition and therefore to reduce the drying time.

Preferably, a ratio of partially hydrolyzed PVA to fully hydrolyzed PVA of 0.5:1 to 2.5:1, most preferably 1.7:1 is used. It is considered that a ratio of 0:1 and 1:0 would give useful dressing or skin-coating materials.

Films of the second hydrophilic polymer alone, such as polyvinyl alcohol alone, formed by evaporation of solutions on the skin, generally have poor adhesion to the skin. This problem is greatly alleviated by mixing the second hydrophilic polymer with polymers of acrylic acid as first hydrophilic polymer eg: polyacrylic acid (PAA). If the molecular weight (MW) of the PAA is too low, optimum physical properties and water resistance of the wound dressing will be adversely affected. On the other hand, low MW grades of PAA make possible higher solids levels in the liquid dressing because of their low viscosity. If the molecular weight of the PAA grade is too high (i.e., 300,000–500,000 or higher), the PAA may be strongly gelled by the addition of certain compounds. It may be advantageous to combine PAA grades of low and intermediate molecular weight. A wide range of combinations are possible within the scope of this invention. Suitable combinations are readily determinable by those skilled in the art, based upon exemplified values given in the specific examples below.

The combination of heat vulcanized PVA and PAA is known in medical research to produce an artificial muscle capable of dilating and contracting with changes in pH (*Nature*, v.189, 381 (1961)).

Preferred plasticizers for use in this invention are propylene glycol, polyhydroxy compounds of low molecular weight including glycerol, sorbitol, gluconolactone, and gluconic acid and urea. A wide range of amounts of plasticizers may be added to the wound dressing or skin coating material, the amounts being evident to those skilled in the art.

In a further embodiment of this invention, the wound dressing or skin coating material comprising the first hydrophilic polymer and the second hydrophilic polymer is mixed with suitable preservatives to improve the shelf life of the product and reduce microbial growth. Many frequently used preservatives known in the art are suitable for use in this invention; however, most preferably sodium benzoate, a common component of fruit juices, and sorbic acid, a common component of cheeses and products thereof, are added.

If it is desired that the water resistance of the wound dressing or skin coating material be further increased, (i.e. a reduction in the loss of polymer and in the development of tackiness following immersion in water) an agent may be added to the material to crosslink the first hydrophilic polymer. An agent that may be used comprises aluminum ion, added in the form of a substantially water-soluble aluminum salt. Aluminum salts which are compatible with humans and animals are widely used such as aluminum chlorhydroxide in underarm deodorants, and ammonium alum as flocculant for clarification of drinking water and in styptic pencils for the treatment of shaving cuts, and may be considered appropriate for use in the present invention. Most preferably, where the first polymer in the material is PAA and the second polymer is PVA, suitable agents to cross-link PAA are ammonium alum $Al(NH_4)(SO_4)_2 \cdot 12H_2O$, potassium alum $AlK(SO_4)_2 \cdot 12H_2O$, sodium alum $AlNa(SO_4)_2 \cdot 12H_2O$, and aluminum sulfate $Al_2(SO_4)_3 \cdot 16H_2O$. Polyvalent cations, including the tetravalent ion zirconium ($Zr^{+4}$) and the divalent ion zinc ($Zn^{-2}$) may effectively cross-link PAA. In addition, iron salts such as ferric sulfate and elements such as magnesium may be used as cross-linking agents.

In a further embodiment of this invention, the wound dressing or skin coating material comprises a drying aid.

In one aspect, the drying aid is an aqueous acid insoluble biocompatible powder which increases the solids level of the composition and may be selected from the group comprising chitin, cross-linked starch, cross-linked gelatin and fully hydrolyzed PVA. This list is not considered exhaustive as other biocompatible materials may be envisaged by one skilled in the art. Chitin is a polysaccharide which forms the cell walls of fungi and the hard shell of insects and crustaceans, and possesses the ability to promote the healing of wounds. To ensure the necessary degree of histocompatibility, the chitin when used should be substantially protein free. The biocompatible powder may also reduce the gloss of the composition, in situ.

In another aspect, the drying aid is a suitable organic solvent. Non-limiting examples of appropriate solvents include ethanol, methanol and isopropanol. The organic solvent increases the fluidity of the dressing material and thereby permits a higher solids level which accordingly reduces the drying time of the composition. Generally, sufficient organic solvent, e.g. ethanol, may be added to give a 0.5-1:1 ratio with water. This ratio may be varied depending on consistency of the dressing material desired and the mode of application of the dressing, as discussed hereinbelow. The addition of too much solvent, e.g. ethanol, may cause precipitation of some of the polymers and settling of dispersed powder during storage of the dressing material. However, within the preferred concentration range, it has been found that ethanol actually prevents aggregation of the biocompatible powder, e.g. starch powder.

In a preferred aspect, the process for producing the hydrogel-forming wound dressing or skin coating material wherein the first polymer is PAA and the second polymer is PVA comprises preparing a homogenous aqueous solution of the first hydrophilic polymer with the second hydrophilic polymer at an elevated temperature and adding, to the resultant solution, at least one plasticizer. The solution is then diluted with alcohol and water and the resultant mixture deaerated.

Accordingly, a preferred process comprises preparing a homogeneous 25% aqueous solution of a mixture of two grades of PAA, 2-6 parts by weight, most preferably 4.1 parts by weight. Subsequently, fully hydrolyzed PVA powder is dissolved in the above solution, and then partially hydrolyzed PVA, together comprising 2-6 parts by weight, most preferably 3.8 parts by weight, in the homogeneous mixture, by heating at 90° C. in a covered vessel to reduce the evaporation of water. While still hot, liquid glycerol 1.7 parts by weight, powdered sorbitol 1.8 parts by weight and 1,5-gluconolactone, 1.8 parts by weight are added. Alternatively, the solids may be added directly. The total plasticizer content may be between 13-31% on the total solids level. Most preferably plasticizers comprise 26.5% of the total solids. Optionally, 0.033 parts by weight of granulated sodium benzoate may be added. Ideally, the amount of sodium benzoate may be between 0.001%-0.1%. After the mixture has cooled to between 50-80° C., most preferably 75° C., sorbic acid, 0.03 parts by weight may optionally be added. Once the solution temperature reaches between 45-75° C., most preferably 70° C., appropriate amounts of cross-linked starch powder, 3-7 parts by weight and then ammonium alum powder, 1.7 parts by weight may optionally be included. Alternatively, ammonium alum may be added as a hot glycerol solution (1 part by weight in 1.7 parts by weight glycerol) or as a water solution. In order to attain satisfactory flow properties, portions of water and ethanol or mixtures thereof may be added at room temperature. Bubbles present in the ensuing mixture are then separated by any appropriate means, such as centrifugation.

The PAA, PMA, PIA, PLA or PBA/PVA, PAA, PMA, PIA, PLA or PBA/PVP, PAA, PMA, PIA, PLA or PBA/PEO, and PAA, PMA, PIA, PLA or PBA/P(EO/PO) wound dressing or skin coating materials contemplated as preferred aspects of this invention may be applied as liquid formulations to the wound which will dry on the skin in situ. The ingredients in these dressings and relative amounts of the ingredients are as described herein.

In a preferred aspect, the process for producing the hydrogel-forming wound dressing or skin coating materials comprises mixing an aqueous solution of the first hydrophlilic polymer with an aqueous solution of the second hydrophilic polymer under agitation. The viscous liquid or gum which forms is separated from the aqueous phase, which is discarded. Water occluded (as opposed to dissolved or emulsified) in a viscous liquid can be removed by centrifugation. Water occluded in a gum can be removed by kneading. A suitable organic solvent such as ethanol or isopropanol is mixed with the viscous liquid or gum to convert it to a fluid state. If necessary, heat may be used to dissolve the organic solvent in the viscous liquid or gum. The resultant liquids generally do not gel at room temperature, and in this case gelation controlling agents are not necessary.

It is preferred, in any embodiment in which post-water-immersion-tackiness is a problem, e.g. in a liquid formulation, that a suitable cross-linking agent be added to the polymers. Cross-linking enhances the water resistance and reduces the aforementioned tackiness.

It is also preferred, in any embodiment in which reduced drying time and low viscosity are desired in the wound dressing or skin coating material, e.g. in a liquid formulation, that a drying aid, as described hereinabove, be added. Most preferably, ethanol is added.

It is also preferred in a liquid wound dressing or skin coating material that a suitable glossreducing powder, such as cross-linked starch powder, may be added for aesthetic purposes.

Another preferred embodiment of this invention is a wound dressing or skin coating material for application to minor cuts, burns, abrasions, lesions and the like or for application to healthy skin, comprising effective amounts of polymers or copolymers of acrylic acid, polymers or copolymers of methacrylic acid, polymers or copolymers of itaconic acid, polymers or copolymers of maleic acid or polymers or copolymers of 3-butene-1,2,3-tricarboxylic acid, or combinations thereof, gelatin, suitable plasticizer(s), and water.

Gelatin is a protein material produced by hydrolysis of collagen from animal bones and connective tissues. Gelatin has served as an encapsulating material, a coating for pills, an emulsifying agent, a coating for photographic materials, a bacterial culture medium, a major ingredient of popular desserts, and for many other widely varied uses. Gelatin is completely soluble in water at elevated temperatures and essentially insoluble at ordinary temperatures.

In the embodiment where gelatin is the second hydrophilic polymer and PAA is the first hydrophilic polymer, a range of PAA grades and molecular weights may be used as in the embodiments described. Having the examples herein which recite non-limiting grades and molecular weight ranges of PAA, a skilled worker could readily determine other appropriate grades and molecular weight ranges of PAA that would be suitable for use within the materials of the present invention. Likewise, the determination of suitable grades and molecular weight ranges of the other first hydrophilic polymers is readily within the skill of an artisan in this area.

If gelatin is the second hydrophilic polymer and PAA is the first hydrophilic polymer, cross-linking agents as described above may optionally be added.

Preferred plasticizers are as described hereinabove.

In this embodiment, an organic solvent should be added to dissolve the precipitate which separates when gelatin and PAA are mixed. Ethanol is preferred, but other solvents such as isopropanol are acceptable.

Optionally, preservative(s) and a gloss reducing powder, as described above, may be added to this wound dressing or skin coating material.

In a preferred aspect, the process for producing the hydrogel-forming wound dressing or skin coating comprises mixing an aqueous solution of the first hydrophilic polymer with an aqueous solution of the second hydrophilic polymer under agitation. The resultant gum is separated from the aqueous phase and kneaded to remove occluded water. A suitable organic solvent such as ethanol or isopropanol is mixed with the gum and the resultant mixture heated to convert the gum to a liquid. This liquid may tend to gel at room temperature, in which case a gel retarding agent may be added. Examples of suitable gel retarding agents include calcium chloride and urea.

Accordingly, a preferred process for producing the hydrogel-forming wound dressing or skin coating material wherein the first polymer is PAA and the second polymer is gelatin, comprises mixing a warm aqueous solution of low molecular weight PAA (5–15 parts by weight, most preferably, 10 parts by weight) with a warm aqueous gelatin solution (5–15 parts by weight, most preferably, 10 parts by weight) with continuous stirring. Once the mixture consolidates, the aqueous phase is then decanted by conventional methods, and excess water is removed by kneading the resultant gum, for about 30 minutes. The gum is then mixed with glycerol (2–8 parts by weight, most preferably 5 parts by weight), and optionally with a modest amount of ethanol (2–7 parts by weight, most preferably, 5.0 parts by weight) and heated. In order to control gelation of the material at room temperature, calcium chloride dihydrate (2–6 parts by weight, most preferably 4 parts by weight) may be dissolved in the heated material. Bubbles introduced during mixing may be removed by a suitable process, such as centrifugation.

The PAA, PMA, PIA, PLA or PBA/gelatin wound dressing or skin coating materials contemplated in this invention may be applied as a liquid formulation to the wound or healthy skin which will dry on the skin in situ. The ingredients and their relative amounts are as described herein.

It is preferred, in any embodiment in which reduced drying time is desired in the material, that a drying aid, as described above, be added.

If the material is to be manufactured and used only as a liquid, it is desirable to add a gloss-reducing powder, as described above.

It is to be understood that certain wound dressing or skin coating embodiments of the present invention may result in "emulsion" materials as opposed to "liquid" materials. In particular, it has been found that the PAA/PVP and PMA/PEO embodiments may form water-in-oil emulsions after mixing the two polymer constituents.

The liquid formulation of the wound dressing or skin coating materials of the present invention may be adapted to be applied in other forms. For example, the liquid formulation may be delivered with a suitable inert gas and propellant under pressure in an appropriate vessel to produce an aerosol spray of the material. In some instances, it is not necessary in the aerosol preparation to add a cross-linking agent, drying aid or gloss-reducing powder. Whether these optional ingredients are incorporated into the material depends on the particular properties desired in the aerosol formulation. It is necessary, however, that the preparation to be used in the aerosol vessel be of a sufficiently low viscosity to be propelled effectively through the spray mechanism of the aerosol vessel and that the particle size and dispersion of the optional powder be such that the orifice does not become clogged.

Alternatively, the liquid or emulsion formulation of the wound dressing or skin coating materials may be delivered, optionally under pressure, from a pump or bottle, preferably from a hand-operated spray pump. Other delivery or packaging embodiments for this novel material will become apparent to the skilled artisan and include, but are not limited to, plastic tubes, squeeze bottles or droppers, and pre-coated swabs or tissue.

Due to the permeability and biological inertness of the hydrogel-forming material, the novel materials of this invention are particularly suited for the incorporation therein of a wide variety of chemotherapeutic agents, medicinal agents and additives. For instance, the dressing can contain topical keratolytics such as salicylic acid and the like, or agents which accelerate healing, or agents with anti-microbial or hemostatic activity.

The quantity of medicinal agents, chemotherapeutic agents or additives which can be incorporated into the material will of course depend on the particular agent, its solubility properties and the presence of other additives. In general, however, the agents will be employed in a therapeutic amount.

In a further embodiment of this invention, the hydrogel-forming material may serve as a viral barrier coating. Optionally, anti-viral agents may be included.

When it is desired that the hydrogel-forming materials described herein be used as skin coatings for insect repulsion, sun protection or fragrance delivery, various other ingredients may be associated with the material. In the case of an insect repellent formulation, an appropriate repellent component, such as N,N-diethyl-meta-toluamide may be included. In the case of a sunscreen formulation, a wide variety of sunblocks such as octyl-dimethyl-para-aminobenzoic acid, ethylhydroxypropyl-para-aminobenzoic acid, benzophenone and menthyl salicylate may be incorporated. In the case of a fragrance vehicle, the desired fragrance in an oil, liquid or powder form is dissolved or suspended in the formulation.

It is a recognized problem with many fragrances for personal use that the odour does not persist long enough after application to the body. In some instances, there is a change in the quality of the perceived odour. This is often manifested by the odour being less desirable. It is contemplated within the scope of this invention that the fragrance be incorporated into the hydrogel-forming material, and that the latter material be applied to various parts of the body. The rate of diffusion of the fragrance to the atmosphere is accordingly reduced, thus providing the advantage that the fragrance can be detected for a much longer period. In addition, in some instances, the quality of the fragrance is maintained or even enhanced.

In a further embodiment of this invention, the novel materials described hereinabove are made opaque, optionally with added medicinal agents, for application onto diseased or discoloured skin. There are numerous opacifying means known to those skilled in the art. For example, the bubbles present in the dressing composition, which are removed by an appropriate method for preparation of the transparent material, may be left in to create an opaque material. Optionally, agents such as cosmetic grades of talc, titanium dioxide or ferric oxide may be added. Wound dressing or skin coating materials containing opacifying agents would be suitable for the coverage of discoloured burn wounds, bruises, surgical scars, varicose veins, birthmarks such as Nevus flammeus, as well as unwanted tattoos.

The following examples set out hereinbelow are not intended to be limiting in any way and merely represent a selection of the hydrogel-forming wound dressing and skin coating materials of the present invention.

By way of background, many of the following examples include performance results of the hydrogel-forming material under selected testing conditions. There are two basic sets of tests that were used to evaluate the coatings on healthy skin:
(1) General Application Testing
(2) Water Resistance Testing
  (a) 5 Second Immersion Test
  (b) 4 Minute Immersion Test
  (c) Occlusive Glove Test.

For the General Application Testing, a coating of the hydrogel-forming test material was placed on either the back of the right or left hand, on the inside of the right or left forearm, or on the outside of the right or left lower leg. The characteristics of the material were assessed at 2-minute time intervals and then 1 to 12 hours post-application.

For all three of the water resistance tests, a coating of the hydrogel-forming test material was placed on healthy skin on the backs of the fingers of the test subjects and allowed to dry for at least one hour before the actual test. The same coating may be used for all three tests, but the 4-minute immersion test must be performed last.

5-Second Immersion Test

The adherent coating is immersed in tap water at 35° C. for 5 seconds, removed, shaken once to remove excess water, exposed to the ambient atmosphere for 60 seconds, and then tested for tackiness. The tack test consists of bringing the end of a clean, dry finger in contact with the surface of the coating using very light pressure, and then breaking contact. The surface is then described as either not tacky, very slightly tacky, slightly tacky, moderately tacky, or very tacky. In some cases in which the surface is not tacky, it is very slippery due to a thin layer of polymer solution. Other observations may include a change in the transparency. The tack level is generally re-assessed at 2 minutes after removing the finger from the bath.

4-Minute Immersion Test

The finger bearing the adherent coating is immersed in a bath containing a minimum of 1 litre, preferablY at least 3 litres, of tap water at 35° C. The temperature loss of the water bath is generally so small over the 4-minute test period that external heating to maintain the temperature is not generally necessary. During the 4-minute immersion, the finger is constantly moved. Upon withdrawal from the bath, the finger is shaken once to remove the excess water, and then the tack level of the coating is determined immediately using the procedure as described above for the 5-second immersion test. Other observations may be made at this time, including a change in transparency, decrease in thickness or increase in thickness (swelling). In some of the examples, the finger is exposed to the ambient atmosphere and the tack level is re-assessed at 2 minutes, 4 minutes, and 6 minutes following withdrawal. The coating is allowed to dry completely by continued exposure to the ambient atmosphere for at least 1 hour. Qualitative changes in flexibility as a result of immersion are noted. The changes may be more readily apparent after a further (optional in many examples) 6–24 hour period if cracking of the film occurs at certain stress points such as over a knuckle.

Occlusive Glove Test

A disposable examination glove is placed on the hand bearing the test coating and an elastic band is placed around the glove at the wrist to loosely seal the atmosphere inside the glove. Normal activities are resumed in the ambient atmosphere until tiny water droplets are visible inside the glove (10–15 minutes). The glove is lightly pressed against the dressing and the presence or absence of adhesion is noted. The glove is then removed and the tackiness of the coating surface toward healthy skin is determined using the parameters as described above for the 5-minute immersion test.

The occlusive glove test is very important for establishing the suitability of coatings for use under rubber gloves or in any other circumstance involving a high relative humidity. Both "vinyl" (Beckton, Dickinson, Product #2203) and polyethylene gloves were used.

In the following examples, two grades of polyvinyl alcohol, partially hydrolyzed and fully hydrolyzed, are indicated as constituents of the hydrogel-forming materials. The fully hydrolyzed polyvinyl alcohol (PVA) is Vinol 107 (98.0–98.8 mole % hydrolyzed); the partially hydrolyzed polyvinyl alcohol (PVA) is Vinol 203 (87.0–89.0 mole % hydrolyzed). Both products are low viscosity grades from Air Products & Chemicals, Inc.

In many of the examples, the polyacrylic acid is described only as Acrysol A-1 or Acrysol A-3. Acrysol A-1 is a 25% aqueous solution of PAA having a molecular weight of less than 50,000. Acrysol A-3 is a 25% aqueous solution of PAA having a molecular weight of less than 150,000. Both are products of Rohm & Haas.

Throughout the examples, it is to be appreciated that the particular type of gluconolactone that was used was delta-gluconolactone powder. The starch powder was highly cross-linked.

During the preparation of the hydrogel-forming materials described hereinbelow, samples of the test material were, in some instances, centrifuged. The purpose of the centrifuging step was either to remove the bubbles introduced by stirring or to separate the suspended matter where desired. This suspended matter excludes deliberately suspended matter such as opacifying powders, gloss reducing powders or drying aid powders.

Over centrifuging a particular hydrogel-forming material may lead to settling of the deliberately suspended matter; however, the determination of an appropriate centrifuging time and speed, given the particular centrifuge apparatus being used, is well within the purview of a skilled artisan.

EXAMPLE 1

Hydrogel-Forming Material Comprising: PAA/PVA, Water, Glyoerol and Gelatin Powder In a glass vessel of 400 ml, 100 g of Vinol 107 (Lot #0809242) were dissolved in a mixture of 50 g of glycerol in 200 ml of distilled water by heating with occasional stirring in a hot water bath (80–90°) for approximately 3 hours. Trapped bubbles caused by the occasional stirring were allowed to rise during the final hour and at the end of this time, the foam on the top of the solution, which was quite thick, was removed. The resultant solution formed a strong gel on cooling. 3.1% of this gel was heated with 12.4 g of a 25% aqueous solution of PAA (Polysciences, Inc., cat #0627; Lot #55107; molecular weight <50,000) and stirred until homogeneous.

Thirteen packages of size 12 (20×60 mm) Gelfoam (sponge of cross-linked gelatin from Upjohn Co.) were opened and the foam sponges were torn into sections 20×20 mm and placed in a consumer appliance for grinding coffee beans (Krups 50, type 202). Grinding of the sponges was carried out for approximately 5 minutes. The product was a slightly off-white, fine powder. All of this powder, 0.6 g, was added to the hot, homogeneous liquid. The lumps in this mixture were crushed against the sides and the bottom of the container to ensure complete dispersion. The resultant mixture was white, translucent, and very viscous.

The dressing was slightly difficult to spread, but had good levelling properties. A small amount was spread over healthy skin on the back of a finger. Approximately 7 minutes after application, the material was still tacky. At 15 minutes after application, the material was tacky only in thick areas. At approximately 27 minutes after application, the material was completely dry, very supple and unobtrusive.

The finger on which this material was applied was immersed in water at 35° C. for 5 seconds, shaken to remove the excess, and observed 60 seconds later. It was found to be very tacky. There was some loss of material from the surface when the tack probe was removed. The finger was agitated in water at 35° C. for 4 minutes. The material was found to be not tacky.

EXAMPLE 2

Hydrogel-Forming Material Comprising: PAA/PVA, Glycerol, Water, Sodium Benzoate, Sorbic Acid, Alum and Chitin Powder One hundred and six grams of a 25% aqueous solution of PAA (Polysciences, Inc.; Product #0627, Lot #55107; MW∼50,000) were placed in a 250 ml glass vessel. 37 g of Vinol 107 (Lot #0809242) were added and the mixture was stirred manually to disperse the PVA granules. Dispersion was very rapid. The mixture was covered with a watch glass to minimize the loss of water vapour from the mixture. The mixture was then placed in a water bath in which the temperature was raised to 95° C. and held at between 95-98° C. for 2 hours. During this time, the mixture was not stirred. At the end of this heating, the hot mixture was stirred manually with a rod for several minutes. Heating, without stirring, was continued for a further 1.2 hours. The mixture was removed from the water bath, and the following ingredients were added in the order given below before the liquid mixture had cooled significantly:
(1) a solution of 11 grams of glycerol in 11 ml of distilled water.
(2) a solution of 0.18 g of sodium benzoate in 3 ml of distilled water.
(3) 0.18 g of sorbic acid added in powder form.

The mixture was stirred manually with a rod after each ingredient addition and for about 5 minutes after the final addition. At the end of this time the temperature of the liquid was 55° C. 30 ml of ethanol were added with constant stirring.

In order to decrease the viscosity of this mixture, 10 ml of distilled water and then 5 ml of ethanol, and finally a mixture of 20 ml of distilled water and 10 ml of ethanol were added. The resulting solution had much better flow properties.

Ammonium alum (N.F., Product #220913 from Drug Trading Company) in an amount of 1.0 g was dissolved in 14 ml of distilled water. This ammonium alum solution was added to the hydrogel-forming mixture. The mixture was stirred with a stiff rod to homogenize it. The final mixture was clear and flowed easily. It was allowed to stand for 35 minutes at room temperature. To 27.4 g of this mixture were added 2.5 g of chitin powder (protein-free, finely powdered chitin obtained from Bentech Laboratories, Pleasanton, California) and an additional 5 ml of distilled water were mixed in. The material was centrifuged.

On application to a subject's finger, the material was thick but spreading was not difficult. Thirteen minutes after application the material was moderately tacky. Fifteen minutes after application the material was neither tacky nor soft. The gloss of the material was equivalent to skin itself and, in fact, it was difficult to detect on the skin from a distance.

5-second immersion test: the material had a slight tack.
4-minute immersion test: the material was moderately opaque, not tacky, adhesion was fair to good, had lost adhesion by swelling and buckling only in a relatively small area and had very good water resistance.
Occlusive glove test: a loose fitting polyethylene glove was used. The material showed no adhesion to the polyethylene, nor was it tacky when touched with a finger immediately after removal of the glove.

EXAMPLE 3

Hydrogel-Forming Material Comprising: PAA/PVA, Water, Sorbic Acid, Sodium Benzoate, Starch Powder, Alum, Glycerol and Ethanol To 100 g of a 25% aqueous solution of PAA (Polysciences, Cat #0627, Lot #55107; MW∼50,000) were added 22 g of Vinol 203, (Lot #01081424). The liquid and solid were mixed by brief stirring with a rod and then 13 g of Vinol 107 (Lot #0809242) were added. The resultant mixture was heated in bath at 85-98° C. and intermittently stirred. When the mixture was not being stirred, the container was covered with a watch glass. 14 ml of distilled water were added and the mixture was stirred and heated in a hot water bath (90-98° C.) for approximately 1 hour. The liquid was stirred with a rod for approximately 5 minutes as it cooled in the laboratory atmosphere. Upon cooling, a quasi-gel resulted.

55.7 g of this gel were heated to 75° and the following additions were made:
(1) 0.075 g sorbic acid.
(2) A solution in 2 ml distilled water of 0.075 g sodium benzoate (BDH Chemicals, Product #B30112, Lot #93224/9185).
(3) 15 g of cross-linked starch powder ("Amistar B", St. Lawrence Starch Co., Lot #08275-B).
(4) 10 ml of distilled water.

After each addition, the polymer mixture was stirred.

A solution of 1.0 g ammonium alum N.F. (Drug Trading Co.; Product #220913) in 1.7 g of glycerol was prepared by heating the mixture to approximately 70° C. The hot solution was then added to 23.6 g of the polymer mixture in which the internal temperature had previously been raised to 70° C. The resultant mixture was stirred and 7.5 ml of ethanol were added. The resultant mixture was then centrifuged.

The resultant hydrogel-forming liquid was applied to the finger of a test subject. Seven minutes after application the material was slightly tacky. Four-minute immersion test:

Immediately after removal - no tack; slippery; whitish.
Five minutes after removal - slight tack;
Fifteen minutes after removal - no tack; white haze almost disappeared.

EXAMPLE 4

Hydrogel-Forming Material Comprising: PAA/PVA, Sorbitol, Glycerol, Sodium Benzoate, Sorbic Acid, Starch Powder, Gluconolactone, Ammonium Alum, Water, Ethanol and Polysorbate 50 g of a 25% aqueous solution of PAA (Polysciences Inc., cat #0627, Lot #55107 MW~50,000) and 50 g of Acrysol A-3 were stirred manually with a rod until homogeneous. 6.6 g of Vinol 107 were added and dissolved by heating in a bath at 95-98° C., and 11.2 g of Vinol 203 were dissolved in the mixture. While the solution was still in the bath, the following materials were added in order:
(1) 11.0 g of sorbitol.
(2) 10.9 g of glycerol.
(3) 0.2 g of sodium benzoate.

The mixture was stirred after each addition and was subsequently cooled to 71° C. 0.2 g of sorbic acid were added with manual stirring. When the internal temperature of the mixture was 62° C., 24 g of starch powder were added with constant stirring.

43 5 g of the resultant polymer mixture were heated to 70° C. internally and a warm solution of 2.9 g gluconolactone in 5 ml of distilled water was added. The polymer mixture was stirred manually.

The temperature of the polymer mixture was raised to 70° C. once again, and 3.2 g of crushed ammonium alum N.F. (Drug Trading Co., DT #220913) were added. The mixture was diluted with 15 ml of ethanol and 2 ml of distilled water. 10 ml of the resultant mixture were removed and centrifuged for 1 hour. The hydrogel-forming material was labelled 55-A.

31.8 g of 55-A were transferred to a clean glass vessel and mixed with 1.4 g of polyoxyethylene sorbitan mono-oleate ("Polysorbate 80"; from Polysciences, cat #3300, Lot #K-475). The mixture was covered, stirred and heated to approximately 60° C. It was further diluted with 5 ml distilled water and 12 ml 95% ethanol. The resultant mixture was centrifuged to remove the tiny air bubbles and labelled 76-A.

The hydrogel-forming materials designated 55-A and 76-A were applied to areas of healthy human skin and the following observations made:

TABLE I

| | General Application Testing | | |
|---|---|---|---|
| Sample | 2 min. post-application | 4 min. post-application | 1 hour post-application |
| 55-A | slight tack at light pressure | slight tack at moderate pressure | not tacky |
| 76-A | very tacky at moderate pressure | moderate tack very supple pressure | not tacky; |

It should be noted that with both 55-A and 76-A, b 100% of the original area remained adherent for 8 hours post-application.

TABLE II

| | Water Resistance | | | | |
|---|---|---|---|---|---|
| | 5 second Immersion Test | | 4 min. Immersion Test | | |
| Sample | 1 min. post imersion | 2 min. post imersion | 0 min. post imersion | 2 min. post imersion | 4 min. post imersion |
| 55-A | very slight tack | very slight tack | very slight tack | very slight tack | very slight tack |
| 76-A | slight tack | slight tack | not tacky | very slight tack | not tacky |

EXAMPLE 5

Hydrogel-Forming Material Comprising: PAA/PVA, Water, Dextran, Glycerol, Sorbitol, Starch, Ammonium Alum and Ethanol 100 g of a 25% aqueous solution of PAA (Polysciences Inc., cat #0627. Lot #55107; MW<50,000) were mixed with 11.6 g of Vinol 107 (Lot #0809242) by heating in a bath at 95-98° C. with occasional stirring.

The polymer mixture was heated to 70° C. and 1.0 g of dextran, which had been dissolved by agitation in 4 ml of distilled water at 40° C., was added. The following ingredients were then added:
(1) 2.5 g glycerol;
(2) 2.5 g sorbitol;
(3) 1.3 g Vinol 203;
(4) 4 ml of distilled water.

The internal temperature of the mixture was raised to 68° C. and 6 g of cross-linked starch powder (Amistar B from St. Lawrence Starch, Lot #08275/B) were added. After further heating, the mixture was diluted with 4 ml of distilled water and 2.3 g of crushed ammonium alum N.F. (Drug Trading Co., D.T. #220913) were stirred into the mixture. After removal from the heat, the mixture was diluted with a total of 9 ml of ethanol and 2 ml of distilled water and then centrifuged.

The resultant hydrogel-forming material was applied to an area of healthy, human skin and the following observations were made:

TABLE III

| | General Application Testing | |
|---|---|---|
| 2 min. post-appln. | 4 min. post-appln. | 5 hours post-appln. |
| tacky | slight tack at moderate pressure | >99.5% of area adherent |

TABLE IV

| Water Resistance | | | | |
|---|---|---|---|---|
| 5 Second Immersion Test | | 4 Min. Immersion Test | | |
| 1 min. post immersion | 2 min. post immersion | 0 min. post-immersion | 2 min. post-immersion | 4 min. post-immersion |
| slight tack | slight tack | neither tacky nor slippery | no tack | no tack |

This example illustrates that, in some instances, a polymer in addition to the first and second hydrophilic polymers may be incorporated into the hydrogel-forming material.

EXAMPLE 6

Hydrogel-Forming Material Comprising: PAA/PVA, Glycerol, Sorbic Acid, Sodium Benzoate, Starch, Water, Alum and Ethanol 72 g of Acrysol A-3 (Lot #71784) were diluted with 20 ml of distilled water. 9.4 of Vinol 107 (Lot #0809242) was added at room temperature. The mixture was stirred to disperse the powder and was then covered and placed in a water bath at 95-98° C. for 25 minutes with occasional stirring. 15.8 g of Vinol 203 (Lot #01081424) were added in a similar fashion.

The following ingredients were mixed together in a separate vessel:
(1) 11.0 g of glycerol;
(2) 0.2 g of sorbic acid;
(3) 0.2 g of sodium benzoate;
(4) 2 ml of distilled water.

After the PAA/PVA polymer mixture had cooled to approximately 74° C., the previously mixed ingredients were added with occasional stirring.

When the internal temperature of the mixture was approximately 60° C., 25 g of starch powder ("Amistar B", St. Lawrence Starch Co., Lot #08275-B) were added.

42.4 g of this resultant mixture were heated to 70° C. and 0.6 g of crushed ammonium alum N.F. (Drug Trading Co., #220913) were added. The mixture was quickly stirred. Mobility was attained by the addition of 33 ml of ethanol and 12 ml of distilled water. The mixture was then centrifuged for 40 minutes.

The hydrogel-forming material was applied to an area of healthy human skin and the following observations were made:

TABLE V

| General Application Testing | | |
|---|---|---|
| 3 min. post-application | 8 min. post-application | 5 hours post-application |
| tacky | moderate tack; | 1% of original area detached; no cracks; transparent |

TABLE VI

| Water Resistance 4 minute Immersion Test | | | |
|---|---|---|---|
| 0 min. post-immersion | 3 min. post-immersion | 5 min. post-immersion | 15 min. post-immersion |
| not tacky; very slippery; haze | slight tack | high tack | no tack; haze gone; no detached edges |

It should be noted that 7.5 hours after removal of the subject's finger from the 4 minute immersion test, 96% of the original area of the hydrogel-forming material on the finger remained adherent. No cracks were found at this time. The hand on which the test material had been placed was then washed with soap and warm water. Subsequent to the wash, the test material cracked at some of the major skin creases; however, it was still adherent to most of the original area. It was found that despite the washing, adhesion was still very good.

EXAMPLE 7

Hydrogel-Forming Material Comprising: PAA/PVA, Glycerol, Sorbitol, Gluconolactone, Sodium Benzoate, Sorbic Acid, Water, Alum, Ethanol and Salicylic Acid 50 g of a 25% aqueous solution of PAA (Polysciences, #0627, Lot #55107; MW 50,000) were combined in a glass vessel with 50 g of Acrysol A-3. 8.6 g of Vinol 107 (Lot #0809242) were rapidly stirred into the PAA mixture until dispersed. The entire mixture was then heated to dissolve the PVA in a bath at 95-98° C. with occasional stirring, and then 14.6 g of Vinol 203 (Lot #01081424) were dissolved in the solution.

The following ingredients were combined with the PAA/PVA mixture with manual stirring:
(1) 10.4 g of glycerol USP.
(2) 11.0 g of sorbitol.
(3) 11.0 g of 1, 5-gluconolactone were dissolved in 24 ml of distilled water. After approximately 30 minutes the gluconolactone solution was added to the hot solution of PAA/PVA subsequent to the glycerol and sorbitol additions.
(4) 0.2 g of sodium benzoate.
(5) 0.20 g of sorbic acid was added to the solution resulting from step (4) after the solution had been cooled to 75° C.

2.9 g of ammonium alum N.F. (Drug Trading Co.; #D.T. 220913; crushed with a spatula) were added to 49.1 g of the mixture resulting from the above additions, when this mixture reached a temperature of 71° C.. The mixture was immediately stirred outside of the heating bath with a rod. The mixture was then re-heated to a temperature of 60° C. and a solution of 10.0 g of salicylic acid B.P. (Drug Trading Co.; #D.T. 225193; Lot #680480) in 35 ml of 95% ethanol was added. The mixture was stirred manually after cooling for several minutes and was then reheated to approximately 60° C. The resulting product was then centrifuged.

EXAMPLE 8

Hydrogel-Forming Material Comprising: PAA/PVA, Glycerol, Sorbic Acid, Sodium Benzoate, Starch, Water, Alum, Ethanol and Polyvinyl Pyrrolidone-Iodine Complex (PVP $I_2$ 72 g of Acrysol A-3 (Lot #9-71784) were diluted with 20 ml of distilled water in a glass vessel. 9.4 g of Vinol 107 (Lot #0809242) were added to the PAA at room temperature. The mixture was stirred to disperse the powder and was then covered and placed in a bath at 95-98° C. for 25 minutes. 15.8 g of Vinol 203 (Lot #01081424) were dissolved in the hot solution.

The following ingredients were mixed together in a separate vessel:
(1) 11.0 g of glycerol.
(2) 0.2 g of sorbic acid.
(3) 0.2 g of sodium benzoate.
(4) 2 ml of distilled water.

This mixture was then added to the PAA/PVA solution after the latter solution had cooled to 74° C. When the internal temperature of the solution was 60° C., 5 g of starch powder ("Amistar B", St. Lawrence Starch Co., Lot #08275-8) were added.

To 41.8 g of this mixture were added 12 ml of distilled water with constant stirring for several minutes. Part of this resultant mixture was centrifuged. Both parts of the mixture, that is both the centrifuged and uncentrifuged parts, were heated in a hot water bath until the internal temperature was 70° C. 0.77 g of crushed ammonium alum N.F. (Drug Trading Co., #DT220913) were added and the mixture was stirred. Consistency was improved by the addition of 21 ml of ethanol. The material resulting from the ethanol dilution was then centrifuged and labelled 25-A.

8.5 g of Plasdone K29-32 from GAF Corp. (PVP, also labelled Povidone NF; Lot #G30121B) were dissolved in 50 ml of distilled water. 1.5 g of iodine crystals (Aldrich Chemical Co., Product #20,777-2; Lot #5030JL) were added. When shaken, the iodine dissolved very slowly.

1.0 g of the PVP-$I_2$ solution described above, was added to the PAA/PVA solution designated 25-A. The mixture was stirred with a stiff rod for about 3 minutes and then centrifuged.

A coating of this hydrogel-forming material was placed on a sheet of Handi-Wrap (Dow). The colour was noted as brownish-purple. Approximately 3 days later, this colour had not disappeared during exposure to the laboratory atmosphere. There was no odour of $I_2$ and the material was relatively supple.

EXAMPLE 9

Hydrogel-Forming Material Comprising: PAA/PVA, Glycerol, Sorbic Acid, Sodium Benzoate, Starch, Ammonium Alum, Water, Ethanol, and Iodine 72 g of a 25% aqueous solution of PAA (Polysciences, #0627, Lot #55107) and 20 ml of distilled water were placed in a glass vessel and stirred briefly. 9.4 g of Vinol 107 (Lot #0809242) were added to the PAA mixture at room temperature with rapid stirring. The mixture was then covered and heated in a bath at 95-98° C. for 40 minutes. 15.8 g of Vinol 203 (Lot #01081424) were then dissolved in the hot solution in a fashion to the addition of Vinol 107.

The following components were then added as described hereinbelow:
(1) 11 g of glycerol
(2) 0.20 of sorbic acid
(3) a solution of 0.20 g of sodium benzoate in 2 ml of distilled water
(4) 5.0 g of starch powder ("Amistar B", Lot #08275-B, from St. Lawrence Starch Co.)
(5) 6.2 g of ammonium alum N.F. (Drug Trading Co., Product #220913 which was crushed with a spatula), were added to the mixture resulting from step 4) when this latter mixture was at a temperature of 65° C.
(6) a total of 48 ml (37.5 g) of ethanol.

The resultant mixture was centrifuged for 45 minutes.

A solution of 2.4 g of glycerol in 2 ml of distilled water was added to the mixture with continual stirring for approximately 4 minutes. The hydrogel-forming material was centrifuged and then applied to an area of healthy human skin and the following observations were made:

TABLE VII

| General Application Testing | | |
|---|---|---|
| 5 min. post-appln. | 12 min. post-appln. | 3½ hrs. post-appln. |
| tacky | not tacky | no cracks; adhesion maintained over 99.5% of original area |

TABLE VIII

| Water Resistance 4 minute Immersion Test | | | | |
|---|---|---|---|---|
| 0 min. post-immersion | 2 min. post-immersion | 4 min. post-immersion | 15 min. post-immersion | 2.5 hrs. post-immersion |
| whittish; not tacky; not slippery | slight tack | slight tack | haze disappeared; no tack; | some cracks at knuckle creases |

A portion of the hydrogel-forming material which was not used for the skin tests was transferred to another container.

0.24 g of A.C.S. grade iodine crystals (Aldrich Chemicals; Product #20,777-2) were dissolved in 5 ml of ethanol. The solution was added all at once to 23.8 g of the hydrogel-forming material described above and the resulting mixture was stirred vigorously. In order to increase further the mobility of the mixture, 3 ml of ethanol were stirred in and the material was centrifuged for 30 minutes. A dry coating of this iodine-containing hydrogel-forming material had a dark brown colour.

EXAMPLE 10

Hydrogel-Forming Material Comprising: PAA/PVA, Glycero 1, Sorbitol, Gluconolaotone, Sodium Benzoate, Sorbic Acid, Starch, Distilled Water, Ethanol and Ammonium Alum or Potassium Alum 30 g of Acrysol A-1 were added to 30 g of Acrysol A-3. 5.2 g of Vinol 107 (Lot #0809242) were then added to the PAA mixture. The mixture was covered and heated in a water bath at 95° C. with intermittent stirring until the PVA had dissolved. 8.8 g of Vinol 203 (Lot #01081424) were dissolved in the hot solution.

The following ingredients were then added to the PAA/PVA mixture:
(1) 6.6 g of glycerol USP
(2) 6.6 g of crushed sorbitol
(3) 6.6 g of 1,5-gluconolaotone dissolved in 11 ml of distilled water
(4) 0.12 g of sodium benzoate.

All these additions were made while the PAA/PVA mixture was still in the hot water bath at 95° C.

The internal temperature of the mixture was then lowered to 71° C. and 0.12 g of sorbic acid were stirred in. With the internal temperature lowered to 67° C., 18.3 g of starch powder ("Amistar B" St. Lawrence Starch Co.; Lot #08275-B) were added to the polymer mixture. The hydrogel-forming material thus formed was divided into two 58.9 g portions.

The internal temperature of the first portion was raised to 69° C. 3.5 g of ammonium alum USP (Drug Trading Co. D.T. #003251 ground to a fine powder) were added. The alum was stirred into the mixture as quickly as possible. The mixture was then diluted with 6 ml of ethanol and 5 ml of distilled water. This hydrogel-forming material was labelled 89-A.

The internal temperature of the second portion was raised to 69° C. 3.7 g of potassium alum (BDH Chemicals, Code #B100009, Lot #99529/5592 ground to a fine powder) were added and the mixture was stirred. The mixture was then diluted with 6 ml of ethanol and 5 ml of distilled water. The resultant hydrogel-forming material was labelled 90-A.

Each of the hydrogel-forming materials 89-A and 90-A were applied to healthy normal skin and the following observations were made:

TABLE IX

| | General Application Testing | | |
|---|---|---|---|
| Sample | 2 min. post-appln. | 4 min. post-appln. | 6 min. post-appln. |
| 89-A | tacky | slight tack | slight tack |
| 90-A | tacky | still tacky | still tack |

TABLE X

| | Water Resistance | | | | | |
|---|---|---|---|---|---|---|
| | 5 second Immersion Test | | | 4 min. Immersion Test | | |
| Sample | 1 min. post-imm'n | 2 min. post-imm'n | 0 min. post-imm'n | 2 min. post-imm'n | 4 min. post-imm'n | 3 hrs. post-imm'n |
| 89-A | slight tack; | no tack | no tack | no tack | no tack | slight detachment; some cracks |
| 90-A | slight tack; | no tack | no tack; | -no tack | no tack | some cracking; some detachment |

EXAMPLE 11

Hydrogel-Forming Material Comprising: PAA/PVA, Glycerol, Sorbitol, Gluconolactone, Sodium Benzoate Sorbic Acid, Distilled Water, Starch, Ammonium Alumn and optionally Isopropanol or Ethanol 60 g of Acrysol A-1 and 60 g of Acrysol A-3 were mixed together. 10.4 g of Vinol 107 (Lot #0809242) were added to the PAA solution. The resultant mixture was covered and heated in a water bath at 95° C. with intermittent stirring until the PVA had dissolved. 17.6 g of Vinol 203 (Lot #01081424) were dissolved in the hot solution.

The following ingredients were then added to mixture as described hereinbelow:
(1) 13.2 g of glycerol USP
(2) 13.2 g of crushed sorbitol
(3) 13.2 g of 1,5-gluconolactone dissolved in 22 ml of distilled water
(4) 0.24 g of sodium benzoate.

All of these additions were made to the mixture while it was still in the hot water bath at 95° C. The internal temperature was then lowered to 71° C. and 0.24 g of sorbic acid was stirred in. The resultant hydrogel-forming mixture was divided into four 49.5 g portions.

6 ml of distilled water were added to the first portion and the internal temperature was raised to 68° C. 9.1 g of starch powder ("Amistar B" St. Lawrence Starch Co., Lot #08275-B) were added with constant stirring. 3.5 g of ammonium alum U.S.P. (Drug Trading Co. D.T. #003251 ground to a fine powder) were added. The alum was stirred into the mixture as quickly as possible, the mixture was diluted with 20 ml of water and the resultant mixture was labelled 75-A. A sample of 75-A was centrifuged to remove the bubbles.

To the second 49.5 g portion of the original PAA/PVA mixture were added 6 ml of isopropanol (BDH Chemicals Analar; water 0.2%, Lot #39721). The internal temperature of the mixture was raised to 68° C. and 9.1 g of starch powder ("Amistar B" St. Lawrence Co., Lot #08275-B) were added all at once with constant stirring. 3.5 g of ammonium alum USP (Drug Trading Co. D.T. #003251 ground to a fine powder) were added. The mixture was stirred and then diluted with 8 ml of isopropanol. The resultant mixture was centrifuged and labelled 76-A.

The internal temperature of the third 49.5 g portion of the original PAA/PVA mixture was raised to 68° C. 9.1 g of starch powder (as above) were added with constant stirring. 3.5 g of ammonium alum USP (as above) were added. The mixture was stirred, diluted with 5 ml of isopropanol and 7 ml of distilled water, centrifuged and labelled 77-A.

The internal temperature of the fourth 49.5 g portion of the original PAA/PVA mixture was raised to 68° C. Starch powder and ammonium alum were added to this portion as described hereinabove. The resultant mixture was then diluted with 4 ml of ethanol and 3 ml of water, centrifuged and labelled 78-A.

Each of the hydrogel-forming materials 75-A, 76-A, 77-A and 78-A were applied to healthy skin and the following observations were made:

TABLE XI

| | Water Resistance | | | | | | |
|---|---|---|---|---|---|---|---|
| | 5 second Immersion Test | | 4 minute Immersion Test | | | | |
| Sample | 1 min. post imm'n | 2 min. post imm'n | 0 min. post imm'n | 2 min. post imm'n | 4 min. post imm'n | 10 min. post imm'n | 1 hr. post imm'n |
| 75-A | | slight tack | not tacky | not tacky | not tacky | not tacky | some cracking; |
| 76-A | slight tack | slight tack | not tacky; smooth surface | slippery | tacky | very tacky | cracking; some peeling |
| 77-A | slight tack | least tack | not tacky; | slippery | tacky | tacky | no cracks; no peeling |
| 78-A | slight tack | least tack (with rough | not tacky; rough | no tack | slight tack | no tack | cracked; peeling |

TABLE XI-continued

| | Water Resistance | | | | | | |
|---|---|---|---|---|---|---|---|
| | 5 second Immersion Test | | 4 minute Immersion Test | | | | |
| Sample | 1 min. post imm'n | 2 min. post imm'n | 0 min. post imm'n | 2 min. post imm'n | 4 min. post imm'n | 10 min. post imm'n | 1 hr. post imm'n |
| 77-A) | | surface | | | | | |

EXAMPLE 12

Hydrogel-Forming Material Comprising: PAA/PVA, Gluconolactone, Sodium Benzoate, Sorbitol, Sorbic Acid, Distilled Water, Glycerol, Starch, and Ammonium Alum 120 g of the two grades of 25% aqueous PAA and 28 g of PVA were prepared and mixed in the manner described above for Example 11. Unless otherwise indicated, the specific product quality and information is the same as in Example 11. Subsequent additions of
(1) 13.2 g 1,5-gluconolactone
(2) 0.24 g sodium benzoate
(3) 13.2 g sorbitol
(4) 0.24 g sorbic acid
(5) 107 ml distilled water
were then made in accordance with the directions of Example 11. The resultant mixture was divided into four 46.0 g portions.

The internal temperature of the first portion was raised to 75° C. The following additions were made:
(1) 3.3 g of glycerol U.S.P.
(2) 9.1 g of starch powder ("Amistar B", St. Lawrence Starch Co., Lot #08275-B)
(3) 3.5 g of ammonium alum U.S.P. (Drug Trading Co., D.T. #003251 ground to a fine powder) dissolved in 10 ml of hot water.

The mixture was then diluted with 5 ml of ethanol and 5 ml of water. The hydrogel-forming material resulting from the first portion was labelled 67-A.

The internal temperature of the second portion was raised to 68° C. The following additions were made:
(1) 9.1 g of starch powder ("Amistar B", St. Lawrence Starch Co., Lot #08275-B)
(2) 3.5 g of ammonium alum USP (Drug Trading Co. DT #003251 ground to a fine powder) dissolved in 3.3 g of glycerol USP. The ammonium alum was partially dissolved at room temperature and almost completely dissolved in a hot water bath at 80° C.

The mixture was then diluted with 6 ml of ethanol and 6 ml of water. The hydrogel-forming material resulting from the second portion was labelled 68-A.

The third portion was diluted with 3 ml of ethanol and 2 ml of water and then the internal temperature of the mixture was raised to 68° C. The following additions were made:
(1) 3.3 g of glycerol USP
(2) 9.1 g of starch powder ("Amistar B", St. Lawrence Starch Co., Lot #08275-B)
(3) 3.5 g of ammonium alum USP (Drug Trading Co., DT #003251 ground to a fine powder) dissolved in 6 ml of water in a hot water bath at 80° C.

This material was diluted with 8 ml of ethanol and 7 ml of water. The hydrogel-forming material resulting from the third portion was labelled 69-A.

The fourth portion was diluted with 3 ml of ethanol and 3 ml of water and the internal temperature of the mixture was raised to 68° C. The following additions were made:
(1) 9.1 g of starch powder (as above)
(2) 3.5 g of ammonium alum USP (as above) dissolved in 3.3 g of glycerol and 1 ml of distilled water. This alum mixture was heated to 80° C. prior to adding to the fourth portion.

The resulting mixture was diluted with 8 ml of ethanol and 7 ml of water and was labelled 70-A.

Each of the samples was centrifuged.

Each of the four samples was then applied to an area of healthy skin and the following observations were made;

TABLE XII

| | General Application Testing | | | |
|---|---|---|---|---|
| Sample | 2 min. post-appln. | 4 min. post-appln. | 6 min. post-appln. | 1 hr. post-appln. |
| 67-A | very tacky | very tacky | tacky | least glossy |
| 68-A | very tacky | very tacky | tacky | some gloss |
| 69-A | very tacky | very tacky | tacky | some gloss |
| 70-A | very tacky | very tacky | slight tack | most glossy |

TABLE XIII

| | Water Resistance | | | | | |
|---|---|---|---|---|---|---|
| | 5 Second Immersion Test | | 4 Minute Immersion Test | | | |
| Sample | 1 min. post imm'n | 2 min. post imm'n | 0 min. post imm'n | 4 min. post imm'n | 4 min. post imm'n | 1 hr. post imm'n |
| 67-A | slight tack | less tack | not tacky; rough surface | no tack | no tack | slight crack; slight peeling |
| 68-A | slight tack | little less tack | not tacky; rough surface | no tack | very slight tack | no cracks; no peeling; |
| 69-A | slight tack | little less tack | not tacky; rough surface | no tack | slight tack | no cracks; no peeling; |
| 70-A | slight tack | little less tack | not tacky; rough surface | no tack | slight tack | no cracks; no peeling |

EXAMPLE 13

Hydrogel-Forming Material Comprising: PAA/PVA, Potassium Hydroxide, Glycerol, Sorbitol, Gluconolactone, Sodium Benzoate, Sorbic Acid, Starch, Ammonium Alum, Distilled Water and Ethanol 30 g of Acrysol A-1 and 30 g of Acrysol A-3 were placed together in a glass vessel with constant stirring. 4 ml of a 10% solution of potassium hydroxide (BDH Chemicals Product #B10210, Lot #84277/5804) were added to this mixture and stirred in to reduce the acidity. The initial pH value of the mixture was 1.5. After the potassium hydroxide addition, the pH was 3.0.

5.2 g of Vinol 107 (Lot #0809242) were added and the mixture was covered and heated in a water bath at 95° C. with intermittent stirring until the PVA had dissolved. 8.8 g of Vinol 203 (Lot #01081424) were added to the hot polymer mixture and dissolved by continued heating in the hot bath at 95° C. with intermittent stirring. The following ingredients were then added in order:
(1) 6.6 g of glycerol USP
(2) 6.6 g of crushed sorbitol
(3) 6.6 g of 1,5-gluconolactone dissolved in 10 ml of distilled water
(4) 0.12 g of sodium benzoate.

The internal temperature of the mixture was lowered to 69° C. 0.12 g of sorbic acid were stirred in. With the internal temperature at 68° C., 18.3 g of starch powder ("Amistar B", St. Lawrence Starch Co., Lot #08275-B) were added. The internal temperature was then maintained at 66° C. and 7.0 g of ammonium alum (as in Example 12) were added. Lastly, the mixture was diluted with 30 ml of ethanol and centrifuged.

The hydrogel-forming material was then applied to an area of healthy skin and the following observations were made:

TABLE XIV

| General Application Testing | | | |
|---|---|---|---|
| 2 min. post-appln. | 4 min. post-appln. | 6 min. post-appln. | 12 min. post-appln. |
| slightly tacky | slightly tacky | slightly tacky | no tack |

TABLE XV

| Water Resistance 4 min. Immersion Test | | | | |
|---|---|---|---|---|
| 0 min. post-imm'n | 2 min. post-imm'n | 4 min. post-imm'n | 6 min. post-imm'n | 1 hr. post-imm'n |
| some swelling; | no tack | no tack | no tack; dry; no gloss | tough; dry; slight cracking |

EXAMPLE 14

Hydrogel-Forming Material Comprising: PAA/PVA, Potassium Hydroxide, Glycerol, Sorbitol, Gluconolactone, Sodium Benzoate, Sorbic Acid, Starch, Distilled Water, Ethanol and Aluminum Sulfate Where the specific product quality and information is not indicated in this example, it is to be assumed that it is the same as in Example 13.

60 g of Acrysol A-1 and 60 g of Acrysol A-3 were placed together in a glass vessel with constant stirring. 9 ml of a 10% potassium hydroxide solution were added to this mixture and stirred in. While the mixture was heated in a water bath at 95° C., 10.4 g of Vinol 107 and 17.6 g of Vinol 203 were added with intermittent stirring until the PVA had dissolved The following ingredients were added in sequence:
(1) 13.2 g of glycerol B.P.
(2) 13.2 g of crushed sorbitol
(3) 13.2 g of 1,5-gluconolactone dissolved in 22 ml of distilled water at 80° C.
(4) 0.24 g of sodium benzoate.

Each of these additions was made while the mixture was in a hot water bath at 95° C.

The internal temperature was lowered to 72° C. and 0.24 g of sorbic acid were stirred in. With the internal temperature at 68° C., 36.6 g of starch powder were stirred in.

59.0 g of this mixture were added to 6 ml of 40% v/v ethanol in water. 2.4 g of aluminum sulfate hexadecahydrate (BDH Chemicals; "Analar" Lot #44368) dissolved in 6 ml of distilled water were added to the mixture at room temperature. Dilution of the mixture was made with 4 ml of 40% v/v ethanol in water and the material was centrifuged.

The hydrogel-forming material was applied to an area of healthy human skin and the following observations were made:

TABLE XVI

| General Application Testing | | | |
|---|---|---|---|
| 2 min. post-application | 4 min. post-application | 6 min. post-application | 2 hours post-application |
| tacky | tacky | moderate tack in thin areas | no cracks; low gloss |

TABLE XVII

| Water Resistance | | | | | | |
|---|---|---|---|---|---|---|
| 5 second Immersion Test | | 4 minute Immersion Test | | | | |
| 1 min. post-imm'n | 2 min. post-imm'n | 0 min. post-imm'n | 2 min. post-imm'n | 4 min. post-imm'n | 6 min. post-imm'n | 5 hr. post-imm'n |
| very slight tack | very slight tack | opaque; no tack | no tack | very slight tack | very slight tack | extensive cracks; adhesion good to very good |

EXAMPLE 15

Hydrogel-Forming Material Comprising: PAA/PVA, Glycerol, Gluconolactone, Sorbitol, Sodium Benzoate, Sorbic Acid, Starch Powder, Distilled Water, Ammonium Alum and Ethanol Two grades of PAA and two grades of PVA were mixed together as indicated in Example 11. The subsequent additions of glycerol, sorbitol, 1,5-gluconolactone, sodium benzoate and sorbic acid were also made in accordance with the amounts and directions of Example 11. Unless otherwise indicated, the specific product quality and information is the same as in Example 11.

With the internal temperature of the resultant mixture at 68° C., 36.6 g of starch powder were added and stirred in.

7.0 g of ammonium alum N.F. (Drug Trading Co., #DT220913, crushed) were stirred into 116.6 g of the polymeric mixture as quickly as possible. The flow properties of the resultant mixture were improved by the addition of 10 ml of distilled water and 12 ml of 95% ethyl alcohol.

EXAMPLE 16

Hydrogel-Forming Material Comprising: PAA/PVA, Glycerol, Sorbitol, Gluconolactone, Sodium Benzoate, Sorbic Acid, Starch Powder, Ammonium Alum, Ethanol and Water - Viral Barrier Testing Two grades of PAA and two grades of PVA were mixed together as indicated in Example 11. The subsequent additions of glycerol, 1,5-gluconolactone, sorbitol sodium benzoate, sorbic acid and starch powder were also made in accordance with the amounts and directions of Example 11. Unless otherwise indicated, the specific product information and quality is the same as in Example 11.

The resultant mixture was heated to an internal temperature of 68° C. and 10.0 g of ammonium alum USP (Drug Trading Co., DT #003251, ground) were added. The mixture was diluted with, in total, 32.5 ml of ethanol and 27.5 ml of water. The material was then centrifuged.

Five circles (11 cm diameter; thickness 0.18-0.20 mm) of Whatman #40 filter paper (W.& R. Balston Limited) were arranged in a row on a levelled surface and secured with tape at the edges. Two spacer bars 1.0 mm thick were placed on either side of, and parallel to, the row of circles. About 25 ml of the hydrogel-forming material were spread over the circles to form a substantially uniform coating using a sheet of stainless steel with a straight edge drawn over the spacer bars. After the coating had dried for 1 day in the ambient atmosphere, test squares 1.5×1.5 cm were cut from the coated filter paper circles and included the attached filter paper. The thickness of these coated test squares was 0.40-0.46 mm. Control squares 1.5×1.5 cm with no coating were cut from circles of Whatman #40 paper from the same box.

Barrier tests were carried out using a cylinder 16 mm deep and 60 mm I.D. having a closed end. The open end was placed on top of a circle of filter paper 60 mm in diameter which had been soaked in cell growth medium and dried. The test squares and control squares were placed on this impregnated paper and treated with a viral suspension as described below.

The impregnated paper was supported by a circular, open mesh of polyethylene, and the mesh was maintained about 10 mm above a bench surface by a metal ring with 4 "legs" to allow free access of air to the underside of the paper.

The virus suspension was of ECHO 11, $TDID_{50}=10^6$. This pico RNA virus was chosen for its small size and hardiness. For the test, 0.1 ml of the suspension was placed on the test or control square. In test Group A, the suspension was left on the square for 10 seconds and then wiped off with a cotton swab. In test Group B, the suspension was not wiped off. Typically, a test run for a single time period consisted of two coated test squares and two control test squares on a circle of paper impregnated with medium. One test and one control square were in Group A and the other test and control squares were in Group B. At the end of the time period, measured from application of the viral suspension, sections (approximately 1.5×1.5 cm) of the impregnated paper beneath the test squares were cut out and tested for the presence of the virus by culturing for 2 days with MRC-5 cells in a suitable medium (MEM).

Detection of Viral Penetration of Hydrogel Barrier: "+" = detected; "−" = not detected

| Test period | Group A (suspension wiped off after 10 seconds) | | Group B (suspension not wiped off) | |
| --- | --- | --- | --- | --- |
| | Hydrogel-coated square | Control square | Hydrogel-coated square | Control square |
| 30 sec. | not determined | + | not determined | + |
| 2 min. | − | + | − | + |
| 5 min. | − | + | − | + |
| 10 min. | − | + | − | + |
| 30 min. | − | + | + | + |
| 1 hr. | − | + | not determined | + |

EXAMPLE 17

Hydrogel-Forming Material Comprising: PAA/PEO, Water, Ethanol and Ammonium Alum 80 g of Polyox WSRN-750 (Union Carbide, Lot #J-856 PEO of MW 300,000) were dissolved in 800 g of distilled water.

This solution was diluted with 600 g of distilled water. To 3/4 or 1,110 g of the resultant solution were added, with vigorous manual stirring, a solution of 240 g of Acrysol A-1 in 250 g of distilled water over a period of 5 minutes.

After standing overnight, a cream coloured semiopaque gum had formed at the bottom of a semiopaque white liquid. The liquid was decanted and the gum was kneaded with a rod for about 15 minutes to express any water.

To 55.3 g of this gum were added 29.9 g of ethanol. After standing overnight, liquid and gum portions had once again separated. The material was loosely covered and stirred occasionally in a bath at 50-60° C. for 1 hour. The material was diluted with a total of 69.2 g of ethanol and 9.6 g of water.

The mixture was then heated in a water bath at approximately 60° C. until the internal temperature was approximately 57° C. A total of 7 g of powdered ammonium alum (BDH Chemicals "Analar" grade, Product #B10007, Lot #10085/4784) were added and the mixture was stirred and heated.

The resultant mixture was diluted in a final stage with 10.6 g of ethanol and 5.6 g of distilled water and then centrifuged. The liquid phase was separated and the sediment discarded.

The resultant hydrogel-forming material was applied to an area of healthy human skin and the following observations were made:

TABLE XVIII

| General Application Testing | | | |
| --- | --- | --- | --- |
| 2 min. post-appl'n. | 4 min. post-appl'n. | 6 min. post-appl'n. | 1 hr. post-appl'n. |
| very tacky | very tacky | slightly tacky | medium gloss; one small crack |

TABLE XIX

| Water Resistance | | | | | | |
|---|---|---|---|---|---|---|
| 5 second Immersion Test | | 4 minute Immersion Test | | | | |
| 1 min. post-imm'n. | 2 min. post-imm'n. | 0 min. post-imm'n. | 2 min. post-imm'n. | 4 min. post-imm'n. | 6 min. post-imm'n. | 3 hrs. post-imm'n. |
| no tack | no tack | no tack | no tack | slight tack | slight tack | no gloss; invisible |

EXAMPLE 18

Hydrogel-Forming Emulsion Material Comprising: PAA/copolymer of PEO, Water, Ethanol, Propylene Glycol and Aluminum Sulfate 100.2 g of Pluronic F108 (BASF copolymer of ethylene oxide/propylene oxide; 14,000; EO/PO=256/54) were dissolved in 552 g of distilled water (unless otherwise indicated, the specific product quality and information is the same as in Example 17).

400.1 g of Acrysol A-1 were added with vigorous stirring to the PEO mixture at room temperature. The resultant mixture after stirring and settling at room temperature consisted of a mobile, clear liquid phase and a translucent, viscous lower layer. The upper liquid layer, which also comprises a foam, was decanted and the lower layer was centrifuged to separate any remaining mobile liquid.

60.9 g of this viscous liquid were placed in a 250 ml glass vessel and 9.8 g of ethanol were added. 4.0 g of aluminum sulfate hexadecahydrate BDH Chemicals, "Analar" grade, Lot #44368) were dissolved in 10.1 g of distilled water and the solution was diluted with 4.1 g of ethanol. The aluminum sulfate solution was then mixed with the polymer solution at room temperature with constant stirring. 1.9 g of propylene glycol U.S.P. were added along with 10.3 g of ethanol. 3.7 g of this material was labelled 13-D. 31.4 g of this material was centrifuged. The sediment and the clear, lower layer were discarded and the top layer was labelled 14-B.

The hydrogel-forming emulsion materials 13-D and 14-B were applied to areas of healthy human skin and the following observations were made:

TABLE XX

| | Water Resistance | | | | | | |
|---|---|---|---|---|---|---|---|
| | 5 second Immersion Test | | 4 minute Immersion Test | | | | |
| Sample | 1 min. post-imm'n. | 2 min. post-imm'n. | 0 min. post-imm'n. | 2 min. post-imm'n. | 4 min. post-imm'n. | 6 min. post-imm'n. | 8 hr. post-imm'n. |
| 13-D | slight tack tack | slight tack | moderate tack | moderate tack | slight tack | very slight | no cracks; adhesion good; very supple |
| 14-B | moderate tack | moderate tack | moderate tack | very tacky | slight tack | very slight tack | no detachment; adhesion good; very supple |

This example shows a hydrogel-forming material comprising a PEO co-polymer which is complexed with PAA. The addition of aluminum sulfate as a cross-linking agent is also exemplified. The material resulting from this example is in the form of a water-in-oil emulsion which was applied to the skin in a similar fashion to the liquid materials.

EXAMPLE 19

Hydrogel-Forming Emulsion Material Comprising: PAA/PEO, Water, Glycerol, Ethanol, Ammonium Alum and Starch Powder 40.2 g of Polyox WSR-N-10 (Union Carbide; PEO MW 100,000; Lot #H-155) were dissolved in 200 g of distilled water (unless otherwise indicated, the specific product quality and information is the same as in Example 17) and the solution was further diluted with 50 g of distilled water.

The solution was stirred while 160.1 g of Acrysol A-1 were added over 30 seconds. Stirring was continued for 5 minutes after the completion of the addition. The clear aqueous phase was decanted and discarded. The viscous phase was centrifuged and the aqueous phase was again discarded.

9.1 g of glycerol were stirred into the mixture at room temperature, followed by 33.1 g of ethanol.

49.5 g of the resultant mixture were transferred to a 250 ml glass vessel and the liquid was heated to 62° C. 4.5 g of powdered ammonium alum were added. While the mixture was still warm, 4.6 g of starch powder were stirred in. A total of 9.4 g of ethanol was added to dilute the mixture.

Part of the resultant mixture was centrifuged and labelled 25-B. Another part of this mixture (34.3 g) was mixed with 4.2 g of starch powder with manual stirring. The material was then diluted with 3.9 g of ethanol, centrifuged and labelled 25-D.

Each of the hydrogel-forming emulsion materials 25-B and 25-D were applied to healthy areas of human skin and the following observations were made:

TABLE XXI

| | General Application Testing | | | |
|---|---|---|---|---|
| Sample | 2 min. post-appl'n. | 4 min. post-appl'n. | 6 min. post-appl'n. | 8 hr. post-appl'n. |
| 25-D | tacky | slight tack | very slight tack | low gloss; good adhesion; good transparency |
| 25-B | tacky | tacky | slight tack | gloss high; transparency good; good adhesion |

TABLE XXII

| | Water Resistance | | | | | | |
|---|---|---|---|---|---|---|---|
| | 5 second Immersion Test | | 4 second Immersion Test | | | | |
| Samples | 1 min. post-imm'n. | 2 min. post-imm'n. | 0 min. post-imm'n. | 2 min. post-imm'n. | 4 min. post-imm'n. | 6 min. post-imm'n. | 10 hr. post-imm'n. |
| 25-D | no tack | no tack | no tack slight haze | no tack; slight haze | no tack; slight haze | no tack; haze gone | cracked; adhesion good |
| 25-B | very slight tack | very slight tack | no tack | no tack | no tack | no tack | overall appearance very good; some large cracks; no gloss; adhesion good |

EXAMPLE 20

Hydrogel-Forming Material Comprising: PAA/PEO, Water, Glycerol, Ethanol, Ferric Sulfate and Starch Powder The material of the present example was prepared in accordance with Example 19 up to and including the addition of 9.1 g of glycerol and 33.1 g of ethanol to the bottom layer of the viscous liquid of the PAA/PEO complex. Unless otherwise indicated, the specific product quality and information is the same as in Example 19.

49.4 g of the material thus formed were placed in a 250 ml glass vessel and heated to 62° C. 2.2 g of ferric sulfate poWder (Fisher Scientific Co., Product #I-142, Lot #793709, $Fe_2[SO_4]_3 \cdot nH_2O$) were stirred into the liquid with constant stirring While the mixture was still warm, 7.0 g of starch powder along with 37.9 g of ethanol and 0.9 g of water were added.

The material was left to stand overnight at room temperature. It was then stirred intermittently in a bath at 50–60° C. for 30 minutes, appropriately cooled and then centrifuged.

The hydrogel-forming material was then applied to an area of healthy human skin and the following observations were made:

TABLE XXIII

| General Application Testing | | | |
|---|---|---|---|
| 2 min. post-appl'n. | 4 min. post-appl'n. | 6 min. post-appl'n. | 1 hr. post-appl'n. |
| tacky | very slight tack | no tack | no cracks; substantially transparent; not tacky |

TABLE XXIV

| | Water Resistance | | | | | |
|---|---|---|---|---|---|---|
| 5 second Immersion Test | | 4 minute Immersion Test | | | | |
| 1 min. post-imm'n. | 2 min. post-imm'n. | 0 min. post-imm'n. | 2 min. post-imm'n. | 4 min. post-imm'n. | 6 min. post-imm'n. | 9 hr. post-imm'n. |
| no tack | no tack | no tack | no tack | no tack | no tack | reasonably transparent; extensively cracked |

EXAMPLE 21

Hydrogel-Forming Emulsion Material Comprising: PAA/PVP, Water, Ethanol, Propylene Glycol and Urea 100 g of Plasdone K29-32 (PVP, also labelled Plasdone NF from GAF Corporation, Lot #G-90504B-54) were dissolved in 400 ml of distilled water. 400 g of Acrysol A-1 were diluted with 400 g of distilled water. The PVP solution, in a 2-litre Pyrex glass measuring vessel was stirred manually as the PAA solution was slowly added. With continued stirring for approximately minutes, a pale yellow liquid separated from the fibrous mass. The liquid was decanted and the fibrous mass was compressed with a stirring rod in a kneading motion as further liquid was expressed. Kneading was continued at intervals over the next 2 hours until the precipitate was a stiff, non-tacky, cream-coloured gum. Stirring and manipulation of the decanted liquid was continued until it yielded a similar gummy material.

The two portions of gummy material were combined and cut into small pieces with a pair of scissors and placed in a 500 ml vessel with 65 g of ethanol. The mixture was loosely covered and kept in a water bath at 75° C. for 1.4 hours and then heated at between 65–75° C. for an additional hour. The material was left to stand overnight.

The next day the material was covered and heated in a bath at 75° C. for 2 hours with constant stirring. The mixture was then diluted with 156 g of ethanol and 19.5 g of distilled water and the mixture was heated in a bath at 70–75° C. for 2 hours without stirring.

170.2 g of this mixture were placed in a 500 ml glass vessel and 25.0 g of propylene glycol USP were added. 18.0 g of urea (BDH Chemicals, "Analar" grade, Product #B10290, Lot #99795/4060) were stirred into the mixture. Further dilutions with 16.8 g of ethanol and 2.7 g of distilled water were made after the mixture had been warmed. A further 18.0 g of urea were added and the mixture was stirred at room temperature. A further 9.1 g of propylene glycol USP were added with constant stirring at room temperature.

The material resulting from these additions was centrifuged and the top layer of clear mobile liquid was discarded. The bottom layer was the hydrogel-forming emulsion material.

This emulsion material was applied to areas of healthy human skin and the following observations were made:

TABLE XXV

| General Application Testing | | | | |
|---|---|---|---|---|
| 2 min. post-appl'n. | 4 min. post-appl'n. | 6 min. post-appl'n. | 2 hr. post-appl'n. | 7 hr. post-appl'n. |
| tacky | slight to moderate tack | slight tack | no loss of adhesion; no cracks; very slight tack | no loss of adhesion; no cracks; very slight tack |

TABLE XXVI

| Water Resistance | | | | | | |
|---|---|---|---|---|---|---|
| 5 second Immersion Test | | | 4 minute Immersion Test | | | |
| 1 min. post-imm'n. | 2 min. post-imm'n. | 0 min. post-imm'n. | 2 min. post-imm'n. | 4 min. post-imm'n. | 6 min. post-imm'n. | 3 hr. post-imm'n. |
| moderate tack | very slight tack | opaque white; no tack | slight tack | slight tack; partially clear | very slight tack; | clear; few medium cracks; no detached areas; adhesion very good |

The hydrogel-forming emulsion material of this example shows that a cross-linking agent need not be added in all of the embodiments of this invention to obtain reasonably good water resistance.

EXAMPLE 22

Hydrogel-Forming Emulsion Material Comprising: PAA/PVP, Water, Ethanol and Glycerol The material of the present example was prepared in accordance with Example 21 described hereinabove up to and including the addition of 163 g of ethanol and 19.5 g of water to the PAA/PVA gummy complex. Unless otherwise indicated, the specific product information and quality is the same as in Example 21.

170.4 g of the material thus formed were placed in a 500 ml glass vessel and heated at approximately 85° C. with frequent stirring. The material was cooled and 53.6 g were transferred to a 300 ml glass vessel. A solution of 8.0 g of glycerol in 13.5 g of ethanol was added at room temperature. The mixture was stirred in a bath at approximately 70° C., cooled, and centrifuged.

The hydrogel-forming emulsion material was then applied to an area of healthy human skin and the following observations were made:

TABLE XVII

| General Application Testing | | | | |
|---|---|---|---|---|
| 2 min. post-appl'n. | 4 min. post-appl'n. | 6 min. post-appl'n. | 2 hr. post-appl'n. | 7 hr. post-appl'n. |
| slight tack | very slight tack; soft | very slight tack | no loss of adhesion; no cracks; no tack | 2% of area detached; medium crack; no tack |

TABLE XXVIII

| Water Resistance | | | | | | |
|---|---|---|---|---|---|---|
| 5 second Immersion Test | | | 4 minute Immersion Test | | | |
| 1 min. post-imm'n. | 2 min. post-imm'n. | 0 min. post-imm'n. | 2 min. post-imm'n. | 4 min. post-imm'n. | 6 min. post-imm'n. | 3 hr. post-imm'n. |
| slight tack | no tack | opaque white; | slight tack | very slight | no tack; partially clear | clear; 1 crack; 5% of area detached; poor flexibility |

This example illustrates a hydrogel-forming material with good water resistance having no cross-linking agent.

EXAMPLE 23

Hydrogel-Forming Material Comprising: PAA/Gelatin Water, Glycerol and Ethanol 60 g of gelatin, USP, Bloom 275 (Canada Packers "Gelrite" Type A porcine hide gelatin, Lot #B647) were dissolved in 400 g of distilled water. 240 g of Acrysol A-3, were diluted with 200 g of distilled water and the internal temperature was raised to 60° C.

The internal temperature of the gelatin mixture was raised to 45° C. The diluted PAA at 45° C. was added quickly to the gelatin solution at 45° C. with constant electric mixing.

152.4 g of the resultant mixture were stored at room temperature. After storage, 2.0 g of rejected water were discarded. There was no evidence of microbial growth. 16.3 g of glycerol BP and 20.2 g of ethanol were added. The mixture was kept in a water bath at 60-65° C. for 25 minutes and then stirred with a rod. A further 5.7 g of ethanol were added.

EXAMPLE 24

Hydrogel-Forming Material Comprising: PAA/Gelatin, Water, Glycerol, Ethanol, Calcium Chloride & Optionally Ammonium Alum The material of the present example was prepared in accordance with Example 23 up to and including the addition of the glycerol and ethanol to the PAA/gelatin complex. Unless otherwise indicated, the specific product quality and information is the same as in Example 23.

The material thus formed was divided into three portions.

To 179.4 g of the complex prepared as in Example 23 were added 13.3 g of calcium chloride dihydrate as a granular solid (BDH Chemicals; Analar grade; Product #B10070; Lot #96660/9711).

A first portion, 29.1 g of this complex, was not treated any further and was labelled 64-D.

A second portion, 29.9 g of this complex was placed in a small glass vessel, covered with a watch glass and heated in a water bath at 65° C. for 30 minutes. 2.5 g of powdered ammonium alum (Drug Trading Co., BP grade; #003251; Lot #270486) were stirred into the mixture as rapidly as possible with a stiff rod. The mixture was then diluted with a total of 38.2 g of ethanol and 22.6 g of distilled water and labelled 68-A. 13.3 g of this mixture were centrifuged and labelled 66- B.

A third portion, 29.1 g of this complex, was covered and heated in a bath at 60–70° C. for approximately 30 minutes, after which the internal temperature was approximately 56° C. 1.0 g of powdered ammonium alum (as above) was stirred in as quickly as possible. The mixture was diluted with a total of 27.8 g of ethanol and 24.7 g of water. The material was allowed to stand at room temperature overnight and then a further 8.7 g of ethanol and 3.3 g of distilled water were added. 11.9 g of this mixture were centrifuged and labelled 68-B.

Samples of the hydrogel-forming materials labelled 64-D, 66-B and 68-B were applied to areas of healthy human skin and the following observations were made:

TABLE XXIX

General Application Testing

| Sample | 2 min. post-appl'n. | 4 min. post-appl'n. | 6 min. post-appl'n. | 1 hr. post-appl'n. | 2 hr. post-appl'n. | 10 hr. post-appl'n. |
|---|---|---|---|---|---|---|
| 64-D | still viscous liquid | very tacky | very tacky | — | transparent; glossy; no loss of adhesion | — |
| 66-B | set but tacky | slight tack | no tack | — | no loss of adhesion; no cracks | — |
| 68-B | tacky | tacky stronger gel than at 2 min. | slight tack | transparent; no cracks; no tack; completely adherent | — | no detached areas; no cracks |

TABLE XXX

Water Resistance

| | 5 second Immersion Test | | 4 minute Immersion Test | | | | see below | see below |
|---|---|---|---|---|---|---|---|---|
| Sample | 1 min. | 2 min. | 0 min. | 2 min. | 4 min. | 6 min. | | |
| 64-D | tacky | slight tack | very tacky | very tacky | very tacky | tacky | 1 hr: 1 small crack; no loss of adhesion | |
| 66-B | not tacky | not tacky | not tacky | very slight tack | no tack | no tack | 7 hr.: no loss of adhesion | 13 hr: adhesion excellent |
| 68-B | slight tack | slight tack | very slight tack; whitish | very slight tack | no tack; transparent | no tack | 1.5 hr: no loss of adhesion; good to very good adhesion | |

EXAMPLE 25

Hydrogel-Forming Material Comprising:
PAA/-Gelatin, Water, Ethanol, Glycerol, Calcium Chloride, Ammonium Alum and Starch Powder The material of the present example was prepared in accordance with Example 24. Unless otherwise indicated, the specific product information and quality is the same as in Example 24.

To the material labelled 68-A in Example 24 were added 4.5 g of cross-linked starch powder (Amistar "B", St. Lawrence Starch Co.), and the mixture was stirred for about 7 minutes. The material was diluted with 2.1 g of ethanol and 2.9 g of water and 14.0 g of the resultant mixture were centrifuged.

The hydrogel-forming material was then applied to an area of healthy human skin and the following observations were made:

TABLE XXXI

General Application Testing

| 2 min. post-Application | 4 min. post-Application | 6 min. post-Application | 2 hr. post-Application |
|---|---|---|---|
| tacky but set | slight tack | very slight tack | transparent; slight gloss; no detachment |

TABLE XXXII

Water Resistance

| 5 second Immersion Test | | 4 minute Immersion Test | | | | |
|---|---|---|---|---|---|---|
| 1 min. post-imm'n. | 2 min. post-imm'n. | 0 min. post-imm'n. | 2 min. post-imm'n. | 4 min. post-imm'n. | 6 min. post-imm'n. | 1 hr. post-imm'n. |
| slight tack to very slight tack | slight some opacity | no tack; slight tack | slight tack transparent; very slight tack | almost good | no tack | adhesion good |

In the occlusive glove test, this hydrogel-forming material performed quite well and it was not damaged on removal of the glove. Finger tack was slight.

EXAMPLE 26

Hydrogel-Forming Material Comprising:
PAA/Gelatin, Water, Ethanol, Glycerol and Polyethylene Glycol Unless otherwise indicated in this example, the specific product quality and information is the same as in Example 25.

60 g of gelatin were dissolved in 400 g of distilled water. 240 g of a 25% aqueous PAA solution were diluted with 200 g of distilled water and the internal temperature was raised to 60° C. With the internal temperature of the gelatin solution at 45° C., the diluted PAA at 55° C. was added quickly to the gelatin with continual mechanical mixing. Upon cooling the material separated into a liquid and a gel. The liquid layer was decanted and as much water as possible was squeezed out of the gel to form a gum.

64 g of this complex were heated and the following components were mixed together and added to the PAA/gelatin complex:
(1) 10 g of polyethylene glycol PEG-300
(2) 10 g of 100% ethanol
(3) 4 g of glycerol B.P.

The resultant mixture was then diluted with 10 ml of distilled water and 10 ml of 100% ethanol.

EXAMPLE 27

Hydrogel-Forming Material Comprising:
PAA/Gelatin, Water, Ethanol, Glycerol, Propylene Glycol, PVP, Calcium Chloride, Sodium Benzoate, Sorbic Acid & Chitin Powder 30 g of gelatin (retail grade; Davis Gelatine Co., Bloom #150; Lot #B22451) were dissolved in 240 ml of distilled water in a 1 litre glass vessel. The mixture was heated to approximately 60° C.

120 g of a 25% aqueous solution of PAA (Polysciences Inc.; Product #0627; Lot #55107) were diluted with 150 ml of distilled water giving a solution of 30 g of PAA in 240 ml of distilled water. The PAA solution was warmed to 42° C. and added to the gelatin solution with manual stirring. A precipitate formed. The aqueous phase was decanted and discarded. The gummy precipitate was kneaded for 1 hour and expressed water was discarded.

To 42.3 g of the gummy precipitate were added 1.2 g of glycerol and 2.3 g of propylene glycol. The resulting mixture was heated at 70–80° C. and stirred until homogeneous. While still warm, a solution of 3.0 g of PVP (GAF Corp.; Plasdone K-29-32, Lot #G-30121B) in 7 ml of ethanol was added.

23.4 g of this mixture were heated in a bath at 70–80° C. until it became mobile and 2.0 g of calcium chloride dihydrate (BDH Chemicals; Product #B10070; Lot #96660/9711) were added with manual stirring. After this mixture had cooled, 26.5 mg of sodium benzoate and 24.5 mg of sorbic acid were added as dry powders.

The resulting mixture was heated once again in a bath at 70–80° C. and 1.3 g of protein-free, finely powdered chitin (Bentech Laboratories) were added. The chitin powder dispersed very quickly when the mixture was stirred.

The hydrogel-forming material was applied to an area of healthy human skin and the following observations were made:

TABLE XXXIII

| General Application Testing | | | | |
|---|---|---|---|---|
| 2 min. post-appl'n. | 4 min. post-appl'n. | 6 min. post-appl'n. | 12 min. post-appl'n. | 1 hr. post-appl'n. |
| very tacky | very tacky | slight tack | not tacky; very soft | soft but much improved |

It was found that this material had good adhesion 7 hours after application; however, it was extensively cracked at knuckle joint creases.

EXAMPLE 28

Hydrogel-Forming Material Comprising:
PAA/Gelatin, Water, Propylene Glycol, Ethanol, Calcium Chloride and Chitin Powder A PAA/gelatin complex comprising 20 g of gelatin (Bloom 150) in 140 ml of water and 20 g of PAA in 140 ml of water was prepared in accordance with Example 27. Unless otherwise indicated, the specific product quality and information is the same as in Example 27.

21.8 g of the PAA/gelatin complex thus formed was mixed with 2 g of propylene glycol USP. The mixture was heated in a bath at approximately 80° C. and stirred until homogeneous. 2 ml of ethanol were then added to the clear solution with brief stirring. While still warm, 2 g of calcium chloride dihydrate were added.

The hydrogel-forming material was applied to an area of healthy human skin. The water resistance of the dry coating was quite good. Even after about 10 hand washings with Ivory bar soap, traces of the material still remained on the skin.

EXAMPLE 29

Hydrogel-Forming Material Comprising: PAA/Gelatin and Water

To a solution, at 43°, of 10.5 g of gelatin (retail grade; Davis Gelatine Co., Bloom #150; Lot #B22451) in 50 ml of distilled water was added a solution of 10 g of PAA (MW 5,000) in 96 ml of distilled water at 42° over 15 seconds. A viscous amber liquid separated. The top layer was decanted and discarded.

The PAA/gelatin complex thus formed was applied to an area of healthy human skin and the following observations were made:

TABLE XXXIV

| General Application Testing | | | |
|---|---|---|---|
| 15 min. post-appl'n. | 18 min. post-appl'n. | 24 min. post-appl'n. | ~2 hrs. post-appl'n. |
| moderate tack | slight tack | not tacky; soft in thick areas | film inflexible; cracked in some areas; transparent |

Approximately 6 hours after application, the coating was immersed in lukewarm water for 2 minutes. At the end of this time, it was tacky but still retained excellent adhesion to the area of skin originally covered and showed no sign of dissolution. It was removed without difficulty by "rolling" it off the coated area.

EXAMPLE 30

Hydrogel-Forming Material Comprising:
PAA/Gelatin, Water, Glycerol, Isopropanol and Calcium Chloride A PAA/gelatin complex comprising 10 g of gelatin (Bloom #150) in 50 ml of water and 10 g of PAA (MW<50,000) in 60 ml of water was prepared in accordance with Example 27. Unless otherwise indicated, the specific product quality and information is the same as in Example 27.

To the PAA/gelatin complex thus formed, were added 10 g of glycerol and 20ml of isopropanol (BDH Chemicals; "Analar" grade; Lot #39721). The mixture was stirred in a water bath at approximately 50° C. until it was homogeneous. It was then allowed to stand until the bubbles had risen.

Half of this mixture was heated in a hot water bath until it became very fluid. 17 ml of isopropanol were added with constant stirring for several minutes. The material was left overnight and it set to a gel with significant strength. Upon heating at 75-80° C., the material melted to a translucent liquid. 2.6 g of calcium chloride dihydrate were added and the mixture was stirred manually for 5 minutes.

The hydrogel-forming material, which did not gel at room temperature, was applied to an area of healthy human skin and the following observations were made:

TABLE XXXV

| General Application Testing | | | | |
|---|---|---|---|---|
| 7 min. post-appln. | 15 min. post-appln. | 25 min. post-appln. | 4 hr. post-appln. | ~9 hr. post-appln. |
| slight to moderate tack | slight tack; transparent | slight tack | very flexible; | no tack; no detachment at edges |

TABLER XXXVI

| Water Resistance | |
|---|---|
| 5 minute Immersion Test 1 min. post-imm'n. | 4 minute Immersion Test 0 min. post-imm'n. |
| transparent; very tacky | transparent; soft gum |

The hydrogel-forming material was stored for 2 years at room temperature. After this storage, the material appeared unchanged except for a small, opaque lower layer which was easily re-dispersed by agitation.

EXAMPLE 31

Hydrogel-Forming Material Comprising: PAA/Gelatin, Water, Glycerol, Calcium Chloride, and Ethanol A PAA/gelatin complex comprising 30 g of gelatin (Bloom 150) in 200 ml of water and 30 g of PAA (MW<50,000) in 210 ml of water was prepared in accordance with Example 27. Unless otherwise indicated, the specific product quality and information is the same as in Example 27.

To 22.3 g of the PAA/gelatin complex thus formed were added 2.5 g of glycerol. The mixture was homogenized with heating and stirring. 2.0 g of calcium hloride dihydrate were then added and the mixture became an opaque soft gum on cooling. It was warmed in a bath at 55° C. and then 4 ml of ethanol were added. The material did not gel at room temperature.

EXAMPLE 32

Hydrogel-Forming Material Comprising: PAA/Gelatin, Water, Glycerol and Ethanol 40 g of a 25% of solution of PAA (Polysciences; Category #0627; Lot #55107; MW<50,000) were diluted with 30 ml of distilled water.

10 g of Polypro 15,000 (George A. Hormel & Co.; Lot #294-5; gelatin hydrolysate, MW~15,000) were dissolved in 50 ml of distilled water. When the solution was at a temperature of 23° C. the PAA solution was added with vigorous stirring. A viscous liquid separated. The mobile aqueous phase was decanted and the viscous liquid was kneaded while additional water was decanted. 10 g of glycerol were mixed into the liquid by stirring and heating.

15 ml of ethanol were added and the resultant mixture was heated in a bath at approximately 50° C. until the bubbles had risen to the surface. The mixture was then allowed to cool at room temperature.

The hydrogel-forming material was applied to an area of healthy human skin and the following observations were made:

TABLE XXXVII

| General Application Testing | | | |
|---|---|---|---|
| 4 min. post-appl'n. | 9 min. post-appl'n. | 18 min. post-appl'n. | ~11 hr. post-appl'n. |
| tacky liquid | thick areas still tacky | slight tack | adherent to 100% of original area; transparent; supple |

EXAMPLE 33

Hydrogel-Forming Material Comprising: PAA/Gelatin, Water, Glycerol and Isopropanol A PAA/gelatin complex comprising 10 g of gelatin hydrolysate (Polypro 15,000) in 130 ml of water and 10 g of a PAA solution (MW~300,000 Polysciences, Lot #36668, Cat. #4551) in 50 ml of water was prepared in accordance with Example 32. Unless otherwise indicated, the specific product quality and information is the same as in Example 32.

To the PAA/gelatin complex thus formed were added 10 g of glycerol. The mixture was heated until homogeneous and then cooled to room temperature. 15 ml of isopropanol (BDH Chemical Co., Analar, Lot #39721) were added with additional stirring and heating.

The hydrogel-forming material was applied to an area of healthy human skin and the following observations were made:

TABLE XXXVIII

| General Application Testing | | | | |
|---|---|---|---|---|
| 4 min. post-appln. | 10 min. post-appln. | 24 min. post-appln. | 49 min. post-appln. | 10 hr. post-appln. |
| thin areas not tacky; thick areas slight tack | tack in thick areas diminished | coating soft | soft; supple; transparent | adherent to 100% of original area |

TABLE XXXIX

| Water Resistance | | |
|---|---|---|
| 5 second Immersion Test | 4 minute Immersion Test | |
| 1 min. post-imm'n. | 0 min. post-imm'n. | 23 min. post-imm'n. |
| clear; moderate tack | whitish; translucent but intact and adherent; tacky | clear; transparent; slight tack |

EXAMPLE 34

Hydrogel-Forming Material Comprising: PAA/Gelatin and Water 240 g of Acrysol A-1 were diluted with 200 g of distilled water and the mixture was heated to 47° C. 60 g of gelatin USP (Gelrite 150, Canada Packers, Lot #0175) were dissolved in 404 g of distilled water by stirring and heating. The temperature of the liquid did not exceed 55° C. during the dissolving process. The gelating solution was stirred and maintained at 48° C. The PAA solution at 47° C. was added to the gelatin solution over a period of approximately 1 minute. Stirring of the resulting precipitate was continued for approximately 16 minutes. The material was then left to stand overnight at room temperature. The resulting material consisted of a gummy solid on top of an almost clear liquid which was decanted and discarded.

EXAMPLE 35

Hydrogel-Forming Material Comprising: PAA/Gelatin, Water, Glycerol, Ethanol, Urea, Ammonium Alum and Optionally Starch Powder A PAA/gelatin complex was prepared in accordance with Example 34. Unless otherwise indicated, the specific product quality and information is the same as in Example 34.

44 g of the gummy PAA/gelatin complex thus formed was mixed with 4.7 g of glycerol B.P. and 6.9 g of ethanol. The mixture was loosely covered and heated to approximately 50° C. with intermittent stirring until the mixture became homogeneous. 12.0 g of urea (BDH Chemicals, Product #B10290, Lot #99795/4060) were added.

46.8 g of this mixture were maintained at approximately 60° C. and then 1.4 g of powdered ammonium alum (BDH Chemicals "Analar" grade, Product #B10007, Lot #100085/4784) were added with stirring. The mixture was then diluted with a total of 15.8 g of ethanol and 6.9 g of water and was left to stand at room temperature for 3 hours.

A 21.5 g sample of this material was labelled 62-A. The remainder of the material, 47.6 g, was mixed with 4.3 g of Amistar "B" starch powder (St. Lawrence Starch Co.). A further dilution with 3.6 g of ethanol and 1.3 g of distilled water was made with continual stirring.

23.8 g of this material were transferred to a clean vessel and stirred for approximately 5 minutes with 3.5 g of Amistar "B" starch powder. A further dilution with 2.5 g of ethanol and 0.9 g of distilled water was made. The material was centrifuged and labelled 63-C.

Samples of the hydrogel-forming materials 62-A and 63-C were applied to areas of healthy human skin and the following observations were made:

TABLE XL

| | General Application Testing | | | |
|---|---|---|---|---|
| Sample | 2 min. post-appln. | 4 min. post-appln. | 6 min. post-appln. | 6 hr. post-appln. |
| 62-A | very tacky | very tacky | very tacky | very slight to slight tack; no loss of adhesion; no cracks; transparent |
| 63-C | moderate tack | slight tack | very slight tack | no tack; no areas of lost adhesion; no cracks; transparent |

TABE XLI

| | Water Resistance | | | | | | |
|---|---|---|---|---|---|---|---|
| | 5 second Immersion Test | | 4 minute Immersion Test | | | | |
| Sample | 1 min. post-imm'n. | 2 min. post-imm'n. | 0 min. post-imm'n. | 2 min. post-imm'n. | 4 min. post-imm'n. | 6 min. post-imm'n. | 1.5 hr. post-imm'n. |
| 62-A | slight tack | slight tack | very slight tack; thick areas hazy | very slight tack | very slight tack | no tack | 1 large crack; 3% of original area detached |
| 63-C | no tack | no tack | no tack; thick areas whitish | slight tack | very slight tack | no tack | many cracks; 8% of original area detached |

EXAMPLE 36

Hydrogel-Forming Material Comprising: PAA/Gelatin, Water, Glycerol, Ethanol, Calcium Chloride, Ammonium Alum and Starch Powder A PAA/gelatin complex was prepared as in Example 34. Unless otherwise indicated, the specific product quality and information is the same as in Examples 34 and 35.

To 208 g of the gummy complex resulting from Example 34 were added 22.5 g of glycerol and 21.1 g of ethanol. The material was labelled 33-0.

53.1 g of this material were heated in a water bath until the internal temperature of the solution was 53° C.. 4.1 g of calcium chloride dihydrate (BDH Chemicals, "Analar" grade Product #B10070, Lot #96660/9711) were added with brief stirring. 2.0 g of powdered aluminum ammonium sulfate (BDH Chemicals, "Analar" grade Product #B10007, Lot #100085/4784) were added to the warm mixture and stirred in as quickly as possible. The mixture was cooled and diluted with a mixture of 17.0 g of ethanol and 4.9 g of distilled water.

The resulting material was centrifuged and the beige, translucent liquid which formed was decanted from the white sediment. 5.4 g of crosslinked starch powder (Amistar "B"; St. Lawrence Starch Co.) were added to the liquid at room temperature with manual stirring for approximately 4 minutes. The mixture was then diluted with a total of 4.2 g of ethanol and 2.2 g of water. Once again, the material was centrifuged.

EXAMPLE 37

Hydrogel-Forming Material Suitable for Aerosol Use Comprising: PAA/Gelatin, Water, Ethanol, Calcium Chloride and Ammonium Alum Unless otherwise indicated, the specific product quality and information in this example is the same as in Example 36.

29.7 g of the complex designated 33-0 in Example 36 were loosely covered and heated in a water bath at 60° C. for 30 minutes. 2.3 g of calcium chloride dihydrate were added and the mixture was stirred until the solid disappeared. 1.1 g of powdered ammonium alum were stirred into the warm mixture. Dilution with 23.9 g of water and 50.8 g of ethanol was then effected. The material was centrifuged for 20 minutes and the liquid was decanted from the white sediment.

Some of the liquid was placed in a Drixoral pump spray (container from Drixoral decongestant nasal spray sold by Shering Canada Inc.). When the pump was activated, this particular liquid material was judged too viscous for use in this device.

Accordingly, 84.9 g of the liquid were further diluted with a mixture of 12.1 g of water and 25.6 g of ethanol (ratio 32:68). The material thus formed was loaded into the Drixoral pump spray and the aerosol effluent was judged to be acceptable.

The underside of the wrist of the left hand was held 6 inches above the pump spray and maintained horizontal. Six sprays about 1.5 seconds apart were directed at the skin of the wrist which formed a wet area about 5 centimeters in diameter. The following observations were made:

TABLE XLII

| General Application Testing | | | |
|---|---|---|---|
| 2 min. post-appl'n. | 4 min. post-appl'n. | 6 min. post-appl'n. | 8 min. post-appl'n. |
| tacky | substantially dry; tacky | slight tack | slight tack |

TABLE XLIII

| Water Resistance 4 Minute Immersion Test | | | | |
|---|---|---|---|---|
| 0 min. post-imm'n. | 2 min. post-imm'n. | 4 min. post-imm'n. | 6 min. post-imm'n. | 10 min. post-imm'n. |
| not tacky | not tacky | slight tack | slight tack | no tack |

EXAMPLE 38

Hydrogel-Forming Material Comprising: PAA/Gelatin, Water, Glycerol, Ethanol, Calcium Chloride, Ammonium Alum, and PVA Powder Unless otherwise indicated, the specific product quality and information is the same as in Example 36.

29.4 g of the complex designated 33-0 in Example 36 were loosely covered and heated in a water bath at approximately 60° C. 2.3 g of calcium chloride dihydrate and 1.1 g of powdered ammonium alum were added and the mixture was stirred, cooled and stirred again. The mixture was diluted at room temperature with 9.5 g of ethanol and 3.8 g of distilled water and was centrifuged to remove the sediment. The liquid was decanted into a clean vessel and 8.0 g of PVA (Elvanol 75-15, Lot #L6K024, a fully hydrolyzed medium molecular weight grade of PVA manufactured by DuPont), which had been seived using an 8" #170 mesh (US Standard, aperture 8 microns), were added. A total of 14.4 g of ethanol and 9.9 g of water was then added and the material was centrifuged.

The hydrogel-forming material was applied to an area of healthy human skin and the following observations were made:

TABLE XLIV

| General Application Testing | | | |
|---|---|---|---|
| 2 min. post-appl'n. | 4 min. post-appl'n. | 6 min. post-appl'n. | 3 hr. post-appl'n. |
| moderate tack | very slight tack | no tack; soft | no tack; ~1% original area detached; transparent; no gloss |

TABLE XLV

| Water Resistance | | | | | | |
|---|---|---|---|---|---|---|
| 5 second Immersion Test | | 4 minute Immersion Test | | | | |
| 1 min. post-imm'n. | 2 min. post-imm'n. | 0 min. post-imm'n. | 2 min. post-imm'n. | 4 min. post-imm'n. | 6 min. post-imm'n. | 1.5 hr. post-imm'n. |
| no tack | no tack | no tack | no tack | no tack | no tack | many cracks; 50% of original area detached |

EXAMPLE 39

Hydrogel-Forming Emulsion Material Comprising: PMA/PEO, Water and Ethanol 10.0 g of poly(methacrylic acid) powder (PMA, Polysciences Inc., cat. #578, Lot #213-11) were dissolved in 200 g of distilled water. The PMA solution was added to a solution of 10 g of Polyox WSRN-750 (Union Carbide; Lot #J-856—PEO of MW 300,000) in 350 g of distilled water with vigorous stirring. A fibrous white precipitate formed during the addition.

After standing overnight, the precipitate had formed a solid gel which was subsequently kneaded to remove the occluded water. This produced 28.3 g of a friable solid.

To 13.9 g of this solid were added 15.3 g of ethanol. The mixture was loosely covered and heated in a bath at 50–60° C. for 1 hour with occasional stirring. The material was diluted with 11.3 g of ethanol.

After standing overnight, the mixture was heated briefly in a bath at 50–60° C. and diluted with 6.0 g of ethanol and 2.3 g of distilled water.

The hydrogel-forming emulsion material was applied to an area of healthy human skin and the following observations were made:

TABLE XLVI

| General Application Testing | | | |
|---|---|---|---|
| 2 min. post-appl'n. | 4 min. post-appl'n. | 6 min. post-appl'n. | 1 hr. post-appl'n. |
| moderately tacky | not tacky; transparent | not tacky; | medium gloss; 2 large cracks |

TABLE XLVII

| 5 second Immersion Test | | 4 minute Immersion Test | | | | |
|---|---|---|---|---|---|---|
| 1 min. post-imm'n. | 2 min. post-imm'n. | 0 min. post-imm'n. | 2 min. post-imm'n. | 4 min. post-imm'n. | 6 min. post-imm'n. | 3 hr. post-imm'n. |
| no tack | no tack | no tack; transparent | very slight tack | no tack | no tack | glossy; no detached area |

EXAMPLE 40

Hydrogel-Forming Material Comprising: PMA/Gelatin, Water, Ethanol, Glycerol and Calcium Chloride 30 g of poly(methacrylic acid) (Polysciences Inc., Cat. #0578, Lot #74687) were dissolved in 300 g of distilled water.

The temperature of a solution of 30 g of; gelatin (Gelrite 150 USP, Lot #0175, Canada Packers, Bloom #150), in 200 g of distilled water was adjusted to 46° C. To it was added the warmed (48° C.) PMA solution with vigorous manual stirring. The resultant gel was kneaded with a stiff rod to express as much water as possible; this resulted in a strong, non-tacky cream coloured gum.

61 g of this gum were left to stand overnight and the water which had separated was decanted. 21.2 g of the resultant gum was cut with scissors into small pieces. 3.6 g of glycerol BP and 6.6 g of ethanol were added. The material was loosely covered and placed in a bath at approximately 60° C. and stirred occasionally. 27.1 g of ethanol were added over a period of approximately 3 hours with intermittent stirring. The vessel was uncovered and heated in a bath at 60–70° C. until 7.7 g had evaporated. To 28.5 g of the resulting mixture were added 1.6 g of calcium chloride dihydrate (BDH Chemicals, Product #B10070, Lot #96660-9711).

The hydrogel-forming material was applied to an area of healthy human skin and the following observations were made:

TABLE XLVIII

| General Application Testing | | |
|---|---|---|
| 2 min. post-appl'n. | 4 min. post-appl'n. | 1 hr. post-appl'n. |
| slight tack; soft | very slight tack; soft | high gloss; no tack; no cracks; no detachment |

TABLE XLIX

| 5 second Immersion Test | | Water Resistance 4 minute Immersion Test | | | | |
|---|---|---|---|---|---|---|
| 1 min. post-imm'n. | 2 min. post-imm'n. | 0 min. post-imm'n. | 2 min. post-imm'n. | 4 min. post-imm'n. | 6 min. post-imm'n. | 8 hr. post-imm'n. |
| very slight tack | no tack | opaque white; no tack | no tack | no tack | no tack | 4% of area detached; some cracks |

EXAMPLE 41

Hydrogel-Forming Material Comprising: PMA/PVA, Water, Glycerol and Ethanol 15.0 g of polymethacrylic acid powder (Polysciences Inc., Cat #0578, Lot #74687) were dissolved in 110 g of distilled water. To the solution, while heated in a bath at 87° C., were added 15 g of Vinol 203 (Lot #08050377) as the solid with manual stirring. The solid dissolved quickly and as it did so a gum separated. The resultant gum was maintained in a bath at approximately 87° C. and kneaded with a stirrer for approximately 15 minutes. Upon cooling, the gum was again kneaded and the liquid phase was decanted. 12.6 g of glycerol BP were added to the gum followed by 15.8 g of ethanol and the material was loosely covered and placed in a bath at approximately 60° C. The gum was kneaded from time-to-time over a period of 30 minutes until no gel particles could be detected. The clear, viscous liquid was then diluted with 11.0 g of ethanol.

The hydrogel-forming material was applied to an area of healthy human skin and the following observations were made:

TABLE L

| General Application Testing | | | |
|---|---|---|---|
| 2 min. post-appl'n. | 4 min. post-appl'n. | 6 min. post-appl'n. | 1 hr. post-appl'n. |
| moderate tack | slight tack | slight tack | high gloss; no tack; no cracks; no detachment |

TABLE LI

| 5 second Immersion Test | | Water Resistance 4 minute Immersion Test | | | | |
|---|---|---|---|---|---|---|
| 1 min. post-imm'n. | 2 min. post-imm'n. | 0 min. post-imm'n. | 2 min. post-imm'n. | 4 min. post-imm'n. | 6 min. post-imm'n. | 8 hr. post-imm'n. |
| slight tack | slight tack | hazy; slippery; no tack | very slight tack | moderate tack | very tacky | no tack; very strong; |

TABLE LI-continued

| | Water Resistance | | | | | |
|---|---|---|---|---|---|---|
| 5 second Immersion Test | | 4 minute Immersion Test | | | | |
| 1 min. post-imm'n. | 2 min. post-imm'n. | 0 min. post-imm'n. | 2 min. post-imm'n. | 4 min. post-imm'n. | 6 min. post-imm'n. | 8 hr. post-imm'n. |
| | | | | | | supple; 1% of area detached |

EXAMPLE 42

Hydrogel-Forming Material Comprising: PMA/PVP, Water, Glycerol, Ethanol, and Ammonium Alum 20.0 g of poly(methacrylic acid) (Polysciences Inc., Cat #0578, Lot #74687) were dissolved in 150 g of distilled water.

20.0 g of PVP (Povidone USP; Plasdone K-2932; GAF Corp.; Lot #G-90504-B-54) were dissolved in 150 g of distilled water.

The PMA solution was added to the PVP solution with vigorous manual stirring at room temperature over a period of 30 seconds. The material was left to stand at room temperature which resulted in a separation of a top layer and a lower layer containing settled gel particles. The top layer was decanted and discarded. The bottom layer was centrifuged to remove some of the occluded water.

To this centrifuged bottom layer (105.7 g) were added 7.9 g of glycerol BP and the mixture was heated in an open vessel in a bath at 78° C. with intermittent stirring for approximately 6.5 hours during which time the weight loss was 49.3 g.

While the mixture was still warm, 21.1 g of ethanol were stirred in. After cooling, a small portion of the mixture was centrifuged to remove small bubbles and labelled 33-B.

The remainder of the mixture, 59.2 g, was heated to an internal temperature of 69° C., and 5.0 g of powdered ammonium alum (BDH Chemicals, Analar grade, product #10007; Lot 100085/4784) were added with manual stirring. The mixture rapidly thickened to a very coherent, near gum. When it had cooled to near room temperature, it was stirred with 6.2 g of ethanol. The resulting mixture, which flowed easily, was centrifuged to remove suspended solid. A top layer of foam was skimmed from the centrifuged liquid, which was decanted from the sediment and labelled 34-A.

The hydrogel-forming materials 33-B and 34-A were applied to areas of healthy human skin and the following observations were made:

TABLE LII

| | General Application Testing | | | |
|---|---|---|---|---|
| Sample | 2 min. post-appl'n. | 4 min. post-appl'n. | 6 min. post-appl'n. | 2 hr. post-appl'n. |
| 33-B | tacky, but set | slight tack | very slight tack | transparent; low gloss; 2% of area detached |
| 34-A | tacky, but set | slight tack | very slight to slight tack | 3% of area detached; many large cracks; transparent; medium to high gloss |

TABLE LIII

| | Water Resistance | | | | | | |
|---|---|---|---|---|---|---|---|
| | 5 second Immersion Test | | 4 minute Immersion Test | | | | |
| Sample | 1 min. post-imm'n. | 2 min. post-imm'n. | 0 min. post-imm'n. | 2 min. post-imm'n. | 4 min. post-imm'n. | 6 min. post-imm'n. | 1 hr. post-imm'n. |
| 33-B | slight to moderate tack | slight tack | no tack; slippery; hazy | very tacky | very tacky | slight tack | no tack; transparent; good adhesion |
| 34-B | very slight tack | very slight tack | no tack; very slight haze | no tack | slight tack | very slight tack | no tack; extensively cracked; 10% of area detached; good adhesion |

EXAMPLE 43

Hydrogel-Forming Material Comprising: PMA/PVP, Water, Glycerol, Ethanol, Ammonium Alum, and Titanium Dioxide The specific product quality and information in this example is the same as in Example 42.

14.8 g of the hydrogel-forming material designated 34-A in Example 42 was manually stirred at room temperature with 2.0 g of titanium dioxide powder (J.T. Baker; product #4162; Lot #41177) until the powder was well dispersed. The mixture was diluted by stirring in 1.0 g of ethanol.

This opaque, white hydrogel-forming material was applied to an area of healthy human skin, and the following observations were made:

TABLE LIV

| General Application Testing | | | |
|---|---|---|---|
| 2 min. post-appl'n. | 4 min. post-appl'n. | 6 min. post-appl'n. | 21 hr. post-appl'n. |
| slight tack | very slight tack | very slight tack | good adhesion; many large cracks at stress points; 50% of original area detached |

TABLE LV

| 5 second Immersion Test | | 4 minute Immersion Test | | | |
|---|---|---|---|---|---|
| 1 min. post-imm'n. | 2 min. post-imm'n. | 0 min. post-imm'n. | 2 min. post-imm'n. | 4 min. post-imm'n. | 6 min. post-imm'n. |
| no tack | no tack | no tack | slight tack | no tack | no tack |

Water Resistance (header for Table LV)

EXAMPLE 44

Hydrogel-Forming Material Comprising: PAA Copolymer/ PEO, Water, Ethanol, Ammonium Alum A solution of 100.1 g of Sokalan CP5 powder (sodium salt of a copolymer of acrylic acid and maleic C; acid, MW 70,000; from BASF, Lot #78-0695) in 140 g of distilled water had a pH of 7.5. Concentrated aqueous hydrochloric acid (~37% w/w HCl) was added in portions of 2-10 ml with stirring until the pH had fallen to about 1.7. The solution was diluted with 258 g of ethanol and allowed to stand for 30 minutes in order to allow the precipitated white solid to settle. The hazy liquid was decanted from the white sediment, which was centrifuged in order to recover more liquid from it. The liquid obtained by centrifiguation and the original decanted liquid were combined and diluted with 410 g of acetone. This produced an opacity due to the formation of a relatively small amount of suspended white solid. The suspension was allowed to stand at room temperature for two weeks, after which it was decanted from a small amount of white sediment. The suspension was then placed in an open dish and gently warmed as a current of air was passed over it until the total amount of evaporated solvent was 663 g. The resulting solution, which was hazy but no longer opaque, was diluted with 200 g of distilled water.

One half (244 g) of the above solution was added with manual stirring over 30 seconds to a solution of 40.0 g of Polyox WSRN-80 (PEO of MW 200,000, narrow MW distribution; from Union Carbide; lot I-273) in 400 g of distilled water. The mixture became opaque during the addition. It was stirred for a further two minutes and allowed to stand for 20 hours, after which it consisted of a hazy, mobile top layer, which was discarded, and a translucent, viscous lower liquid layer. After the lower layer had been centrifuged to remove some of the occluded water, it weighed 130.6 g.

65.2 g of the viscous liquid were placed in an open vessel and kept in a bath at 75-80° C. with intermittent stirring until the evaporative weight loss had reached 26.0 g (2 hours). While still warm, the mixture was diluted with a total of 16.5 g of ethanol, added in portions with stirring. The resulting clear, mobile solution was allowed to stand at room temperature for 13 days. While loosely covered, it was then heated in a bath at about 75° C. until the internal temperature reached 67° C, and 6.1 g of powdered ammonium alum (BDH Chemicals; Analar grade; product B100007; Lot 100085/4784) were added. The mixture was stirred manually for three minutes while in the bath and three minutes while out of the bath. The alum addition caused an increase in viscosity. A viscosity suitable for spreading on skin was produced by dilution, in stages, with a total of 21.6 g of ethanol. After centrifuging to settle suspended solid, the translucent liquid was decanted and labelled 43-A.

The hydrogel-forming material was applied to an area of healthy human skin and the following observations were made;

TABLE LVI

| General Application Testing | | | | |
|---|---|---|---|---|
| 2 min. post-appl'n. | 4 min. post-appl'n. | 6 min. post-appl'n. | 16 min. post-appl'n. | 2 hr. post-appl'n. |
| tacky, but set | slight tack | slight to very slight tack | very slight tack; transparent; medium gloss | no tack; no cracks; no detached areas |

TABLE LVII

| 5 second Immersion Test | | 4 minute Immersion Test | | | | |
|---|---|---|---|---|---|---|
| 1 min. post-imm'n | 2 min. post-imm'n | 0 min. post-imm'n | 2 min. post-imm'n | 4 min. post-imm'n | 6 min. post-imm'n | 8 hr. post-imm'n |
| very slight tack | slight tack | no tack; slippery; some loss by dissolution | slight tack | tacky | slight tack | no tack; no cracks; low to medium gloss; very good adhesion |

Water Resistance (header for Table LVII)

EXAMPLE 45

Hydrogel - Forming Material Comprising: PAA Copolymer/PEO, Water, Ethanol, Ammonium Alum, and a Fragrance The specific product quality and information in this example is the same as in Example 44.

To 15.6 g of the hydrogel-forming material 43- A of Example 44 were added 0.5 g of Cachet Spray Cologne (Prince Matchabelli, Markham, Ontario, Canada). The mixture was stirred manually for one minute, and its viscosity was reduced by stirring in a total of 2.7 g of ethanol. The mixture was centrifuged to remove tiny bubbles and was labelled 44-A.

The fragrance delivery capability of the hydrogel-forming skin coating material was compared directly with that of a coating of Cachet Spray Cologne as follows: Two sites 2×3 cm were delineated on the insides of the left and right forearms of a volunteer. To the site on the left arm were spread approximately 0.3 ml of 44-A, and to the site on the right arm were spread 2 drops (approx. 0.1 g) of Cachet Spray Cologne. The results of subjective sniff tests of both sites carried out in an identical manner by the same person at various times following application are given in Table LVIII below. The test sites were kept from contact with water during the total test period.

TABLE LVIII

| | Fragrance Delivery Characteristics | | |
|---|---|---|---|
| Time post-appl'n | Perceived Odour Level | | Comparative Odour Quality |
| | Coating of 44-A | Pure Cachet Spray Cologne | |
| 10 min. | strong | moderate to strong | — |
| 30 min. | moderate | moderate to strong | — |
| 60 min. | moderate | moderate to strong | 44-A more pleasant (less "sharp") |
| 2 hr. | weak to moderate | moderate | 44-A more pleasant (less "sharp") |
| 3 hr. | weak to moderate | moderate | 44-A more pleasant (less "sharp") |
| 5 hr. | weak | weak | 44-A much more pleasant |
| 15 hr. | weak | weak | 44-A much more pleasant |
| 20 hr. | weak | very weak | detection of differences difficult because of weakness of odour from pure Cachet site |
| 27 hr. | weak | extremely weak | detection of differences difficult because of weakness of odour from pure Cachet site |
| 41 hr. | weak | extremely weak | detection of differences difficult because of weakness of odour from pure Cachet site |
| 67 hr. | very weak | not detectable | — |
| 114 hr. | extremely weak | — | — |

EXAMPLE 46

Hydrogel-Forming Material Comprising: PAA copolymer/PEO, Water, Ethanol, Ammonium Alum, and a Fragrance The specific product quality and information in this example is the same as in Example 44.

To 15.6 g of the hydrogel-forming material 43-A of Example 44 were added 0.3 g of Chantilly Purse Perfume (#1404, Houbigant Ltee, Montreal, P.Q., Canada). The mixture was stirred for two minutes using a stiff rod, centrifuged to remove tiny bubbles, and labelled 45-A.

The fragrance delivery capability of the hydrogel-forming skin coating material was compared directly with that of a coating of Chantilly Purse Perfume as follows: two sites 2×3 were delineated on the insides of the calves of the left and right legs of a volunteer. To the site on the left leg were spread approximately 0.3 ml of 45-A, and to the site on the right leg were spread two drops (approximately 0.1 g) of Chantilly Purse Perfume. The results of subjective sniff tests of both sites carried out in an identical manner by the same person at various times following application are given in Table LIX below. The test sites were kept from contact with water during the total test period.

TABLE LIX

| | Fragrance Delivery Characteristics | | |
|---|---|---|---|
| Time post-appl'n. | Perceived Odour Level | | Comparative Odour Quality |
| | Coating of 45-A | Pure Chantilly Purse Perfume | |
| 10 min. | strong | strong | — |
| 30 min. | strong | moderate to strong | 45-A marginally more pleasant than Chantilly |
| 60 min. | moderate to strong | moderate to strong | 45-A marginally more pleasant than Chantilly |
| 3 hr. | weak to moderate | moderate | 45-A marginally more pleasant than Chantilly; 45-A "sweeter" and less "harsh" |
| 5 hr. | weak to moderate | weak | 45-A marginally more pleasant than Chantilly |
| 12 hr. | weak | weak | 45-A marginally more pleasant than Chantilly |
| 20 hr. | weak | weak; a little weaker than 45-A | 45-A marginally more pleasant than Chantilly |
| 32 hr. | weak | weak | — |
| 41 hr. | weak | extremely weak | — |
| 67 hr. | weak | not detectable | 45-A still pleasant |
| 114 hr. | weak | — | 45-A still pleasant |

We claim:

1. A method for making a hydrogel-forming wound dressing or skin coating material, said material comprising a first hydrophilic polymer selected from polymers of acrylic acid, a second hydrophilic polymer which is polyvinyl alcohol, and water, the method comprising:
   (a) preparing a homogenous solution of the first hydrophilic polymer with the second hydrophilic polymer at an elevated temperature;
   (b) diluting the solution produced in step (a) by mixing it with water and an organic solvent; and
   (c) de-aerating the resultant mixture.

2. The method according to claim 1 wherein the first hydrophilic polymer is polyacrylic acid of low and intermediate molecular weight.

3. The method according to claim 1 wherein the second hydrophilic polymer is a mixture of partially and fully hydrolyzed polyvinyl alcohol.

4. The method according to claim 1 including the additional step (d) of adding to the solution of step (a), compatible preservatives.

5. The method according to claim 4 wherein said preservatives are selected from the group consisting of sodium benzoate, sorbic acid and mixtures thereof.

6. The method of claim 1 including the additional step (e) of adding at least one suitable plasticizer to the solution resulting from step (a).

7. The method according to claim 6 wherein the plasticizer is selected from the group comprising glycerol, propylene glycol, sorbitol, gluconolactone and gluconic acid.

8. The method according to claim 6 including the additional step (f) of adding to the preservative containing mixture resulting from step (d), a biocompatible powder.

9. The method according to claim 8 wherein said powder is selected from the group comprising chitin, talc, cross-linked starch and cross-linked gelatin.

10. The method according to claim 8 including the subsequent step (g) of adding to the resultant mixture, a compatible soluble aluminum salt or derivative thereof.

11. The method according to claim 10 wherein said aluminum salt is selected from the group comprising ammonium alum, sodium, alum, potassium alum, and aluminum sulfate.

12. The method according to claim 11 wherein said aluminum salt is ammonium alum.

13. A method for making a hydrogel-forming wound dressing or skin coating material, said material comprising a first hydrophilic polymer selected from polymers of acrylic acid and polymers of methacrylic acid or combinations thereof, a second hydrophilic polymer which is capable of interacting with the first hydrophilic polymer to produce, upon drying, a hydrogel of improved water-resistance and film-forming properties relative to the first polymer alone, and water, the method comprising:
(a) mixing an aqueous solution of the first hydrophilic polymer with an aqueous solution of the second hydrophilic polymer to produce an aqueous phase and a gum or water-immiscible viscous liquid;
(b) removing the aqueous phase;
(c) processing the viscous liquid or gum to remove occluded water; and
(d) mixing the gum or viscous liquid with a suitable organic solvent.

14. The method according to claim 13 wherein the first hydrophilic polymer is polyacrylic acid.

15. The method according to claim 13 wherein the second hydrophilic polymer is selected from gelating, polyvinyl pyrrolidone, polyethylene oxide and copolymers of ethylene oxide and propylene oxide.

16. The method according to claim 13 including the subsequent step (e) of heating the mixture resulting from step (d).

17. The method according to claim 13 including the subsequent step (f) of adding calcium chloride to the mixture from step (e).

18. The method according to claim 13 wherein the organic solvent is selected from isopropanol, ethanol and methanol.

19. The method according to claim 13 wherein the gum or viscous liquid of step (d) is mixed with at least one of glycerol and propylene glycol.

* * * * *